United States Patent
Franzone et al.

(10) Patent No.: US 11,864,587 B2
(45) Date of Patent: Jan. 9, 2024

(54) CAPSULES FOR USE IN PERSONAL VAPORIZERS

(71) Applicant: VALLEY PRODUCT CONCEPTS, LLC, Hunt Valley, MD (US)

(72) Inventors: John B. Franzone, Rockville, MD (US); Leo Kahl, Bel Air, MD (US); Raymond J. Fioravante, Kingsville, MD (US); Raymond H. Fioravante, Kingsville, MD (US); Nicholas Flower, Minneapolis, MN (US)

(73) Assignee: Valley Product Concepts, LLC, Hunt Valley, MD (US)

( * ) Notice: Subject to any disclaimer, the term of this patent is extended or adjusted under 35 U.S.C. 154(b) by 586 days.

(21) Appl. No.: 17/252,463

(22) PCT Filed: Jun. 14, 2019

(86) PCT No.: PCT/US2019/037221
§ 371 (c)(1),
(2) Date: Dec. 15, 2020

(87) PCT Pub. No.: WO2019/241651
PCT Pub. Date: Dec. 19, 2019

(65) Prior Publication Data
US 2021/0307385 A1  Oct. 7, 2021

Related U.S. Application Data

(60) Provisional application No. 62/685,543, filed on Jun. 15, 2018.

(51) Int. Cl.
*A24F 40/20* (2020.01)
*A24F 40/05* (2020.01)
*A24F 40/42* (2020.01)

(52) U.S. Cl.
CPC .............. *A24F 40/20* (2020.01); *A24F 40/05* (2020.01); *A24F 40/42* (2020.01)

(58) Field of Classification Search
CPC ........... A24F 40/20; A24F 40/05; A24F 40/42
(Continued)

(56) References Cited

U.S. PATENT DOCUMENTS

| D150,175 S | 7/1948 | Thomas |
|---|---|---|
| 2,543,190 A | 2/1951 | Musekamp |

(Continued)

FOREIGN PATENT DOCUMENTS

| CH | 707 222 A2 | 5/2014 |
|---|---|---|
| DE | 20 2012 009708 U1 | 11/2012 |

(Continued)

OTHER PUBLICATIONS

International Search Report and Written Opinion of the International Searching Authority for International Application No. PCT/US2019/037221, dated Sep. 9, 2019.

(Continued)

*Primary Examiner* — Alexander Gilman
(74) *Attorney, Agent, or Firm* — Potomac Law Group, PLLC

(57) ABSTRACT

Capsules are provided for holding material within a vaporization chamber of a personal or portable vaporization device. Each capsule comprises a cap and a cup, each with a corresponding base wall having air inlet/outlet holes therein. The capsules are provided with first and second standoff structures that position the respective capsule to avoid occlusion of the air inlet/outlet holes by surfaces of the oven and/or lid that form the vaporization chamber. During use of the vaporization device, the capsule design encourages air to flow through the material held within the capsule via the air inlet/outlet holes, rather than flowing around the (Continued)

capsule to bypass the material held therein. In some embodiments, the capsules include tamper-resistant features that prevent separation of the cap and cup once assembled, thereby protecting the material held within the capsule.

28 Claims, 13 Drawing Sheets

(58) Field of Classification Search
USPC ........................................................ 131/329
See application file for complete search history.

(56) References Cited

U.S. PATENT DOCUMENTS

| | | | |
|---|---|---|---|
| D293,943 S | 1/1988 | Wadsworth | |
| 5,152,284 A * | 10/1992 | Valentini | A61M 15/0033 |
| | | | 128/203.23 |
| D373,846 S | 9/1996 | Rothman | |
| 5,562,918 A * | 10/1996 | Stimpson | A61M 15/0048 |
| | | | 604/890.1 |
| 5,993,520 A | 11/1999 | Yu | |
| 6,065,592 A | 5/2000 | Wik | |
| D449,404 S | 10/2001 | Emery | |
| 6,746,521 B2 * | 6/2004 | Canfield | A61L 9/12 |
| | | | 239/57 |
| D568,533 S | 5/2008 | Bagaric et al. | |
| D592,401 S | 5/2009 | Beavers et al. | |
| 8,215,300 B2 * | 7/2012 | Steiner | A61M 15/0028 |
| | | | 128/203.15 |
| D669,962 S | 10/2012 | Schoenherr et al. | |
| D684,240 S | 6/2013 | Stein | |
| 8,709,337 B2 | 4/2014 | Gruenbacher et al. | |
| D710,543 S | 8/2014 | Dittmer et al. | |
| D712,091 S | 8/2014 | Liu | |
| 8,807,538 B2 * | 8/2014 | Sharma | A01M 1/2033 |
| | | | 261/107 |
| D714,958 S | 10/2014 | Smeja | |
| 8,869,792 B1 | 10/2014 | Lee | |
| 8,938,159 B2 | 1/2015 | Hsiao | |
| 8,950,397 B2 * | 2/2015 | Steiner | A61M 15/0025 |
| | | | 128/203.15 |
| D734,867 S | 7/2015 | Smeja | |
| 9,272,103 B2 | 3/2016 | Storz | |
| 9,408,416 B2 | 8/2016 | Monsees et al. | |
| D779,045 S * | 2/2017 | Johansen | D23/261 |
| D794,082 S | 8/2017 | Krull | |
| D800,286 S | 10/2017 | McKay et al. | |
| D806,850 S | 1/2018 | D'Amico | |
| D816,434 S | 5/2018 | Burns | |
| 10,010,687 B2 * | 7/2018 | Von Schuckmann | |
| | | | A61M 15/0026 |
| D831,172 S | 10/2018 | Schluter | |
| D835,841 S | 12/2018 | Xu | |
| D868,367 S | 11/2019 | Franzone et al. | |
| D868,368 S | 11/2019 | Franzone et al. | |
| D869,087 S | 12/2019 | Franzone et al. | |
| D870,371 S | 12/2019 | Storz | |
| D880,675 S | 4/2020 | Gobber et al. | |
| D903,192 S | 11/2020 | Chang et al. | |
| 10,834,964 B2 * | 11/2020 | Monsees | A24F 13/04 |
| D950,030 S * | 4/2022 | Flower | D23/360 |
| 2003/0111552 A1 * | 6/2003 | Vedrine | A61M 5/284 |
| | | | 239/533.1 |
| 2004/0159322 A1 * | 8/2004 | Kladders | A61M 15/0028 |
| | | | 128/203.15 |
| 2004/0182387 A1 * | 9/2004 | Steiner | A61M 15/0028 |
| | | | 128/203.15 |
| 2007/0283972 A1 | 12/2007 | Monsees et al. | |
| 2010/0331765 A1 * | 12/2010 | Sullivan | A61M 15/0056 |
| | | | 604/93.01 |
| 2014/0137865 A1 * | 5/2014 | Seeney | A61M 15/0028 |
| | | | 128/203.15 |
| 2014/0174441 A1 * | 6/2014 | Seeney | A61M 15/0028 |
| | | | 128/203.15 |
| 2014/0182587 A1 * | 7/2014 | Dunne | A61M 15/0043 |
| | | | 128/203.15 |
| 2014/0318539 A1 * | 10/2014 | Chan | A61M 15/0028 |
| | | | 128/203.15 |
| 2017/0035115 A1 | 2/2017 | Monsees et al. | |
| 2017/0055574 A1 * | 3/2017 | Kaufman | A24F 40/465 |
| 2017/0156403 A1 | 6/2017 | Gill et al. | |
| 2017/0231283 A1 | 8/2017 | Gadas | |
| 2017/0311384 A1 * | 10/2017 | Wu | A61M 11/042 |
| 2017/0319797 A1 * | 11/2017 | Germinario | A61M 15/002 |
| 2017/0325504 A1 * | 11/2017 | Liu | A61M 11/042 |
| 2018/0064839 A1 * | 3/2018 | Hsiao | A61L 9/03 |
| 2018/0085551 A1 * | 3/2018 | krietzman | H05B 1/0252 |
| 2018/0279678 A1 * | 10/2018 | Hepworth | A24F 40/42 |
| 2019/0230990 A1 * | 8/2019 | Hepworth | A24D 3/061 |
| 2021/0307385 A1 * | 10/2021 | Franzone | A61M 15/0028 |

FOREIGN PATENT DOCUMENTS

| | | |
|---|---|---|
| WO | WO 2015/116934 A1 | 8/2015 |
| WO | WO 2016/172802 A1 | 11/2016 |
| WO | WO 2018/0069675 A1 | 4/2018 |

OTHER PUBLICATIONS

Extended European Search Report for European Patent Application No. 19820091.7, dated Mar. 3, 2022.
BudKup Gen. 1.0, available online via e-commerce website (https://www.budkups.com), Mar. 2, 2017.
BudKup Gen. 1.5, available online via e-commerce website (https://www.budkups.com), May 2, 2018.
BudKup Gen. 2.0, available online via e-commerce website (https://www.budkups.com), Feb. 14, 2018.
European Union Intellectual Property Office, Industrial Design 003387299-0001, "Container for Medical Purposes," published Sep. 2016.
FlowerMate Accessories [online], Jun. 7, 2018 [retrieved May 3, 2019]. Retrieved from the Internet: <https://flowermate.com/product-category/accessories/>.
Ghost Vapes Accessories [online], Oct. 2017 [retrieved on May 30, 2019]. Retrieved from the Internet: <https://web.archive.org/web/20171016181457/https://www.ghostvapes.com/accessories>.
Storz & Bickel Dosing Capsule Set [online], Jun. 7, 2018 [retrieved May 3, 2019]. Retrieved from the Internet: <https://www.storz-bickel.com/us/en/dosing-capsule-set-40.html>.

* cited by examiner

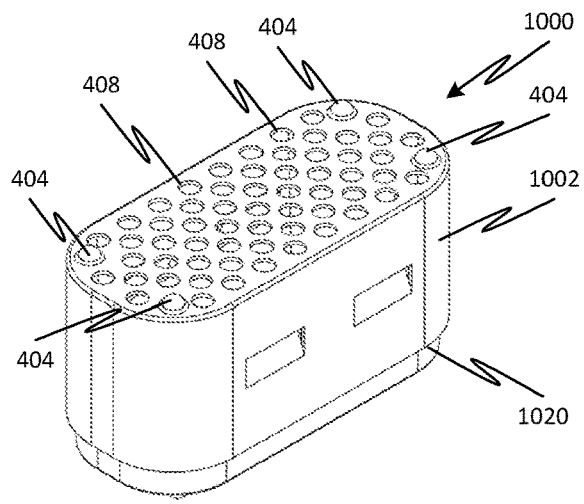
FIG. 10A
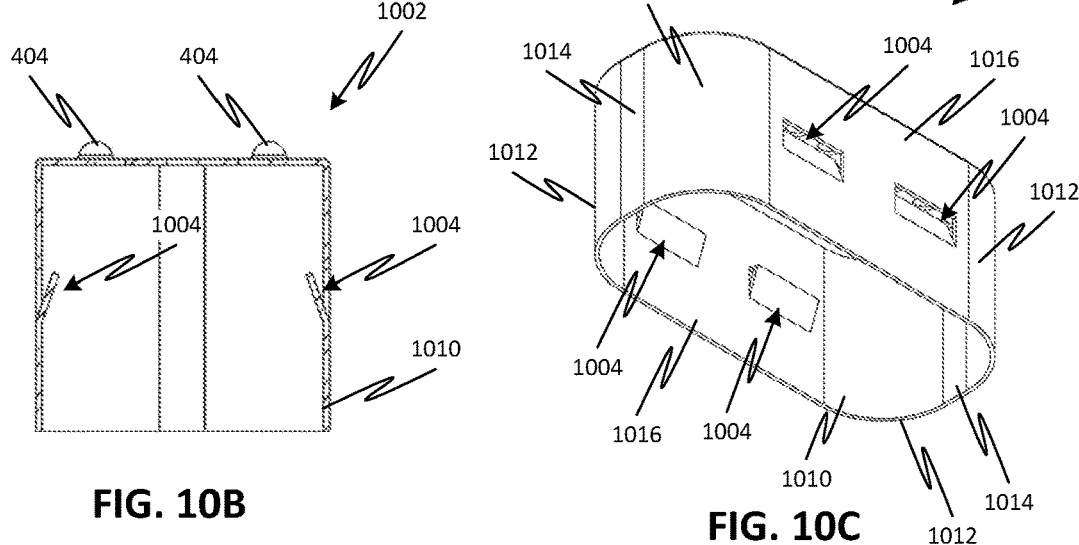
FIG. 10B
FIG. 10C
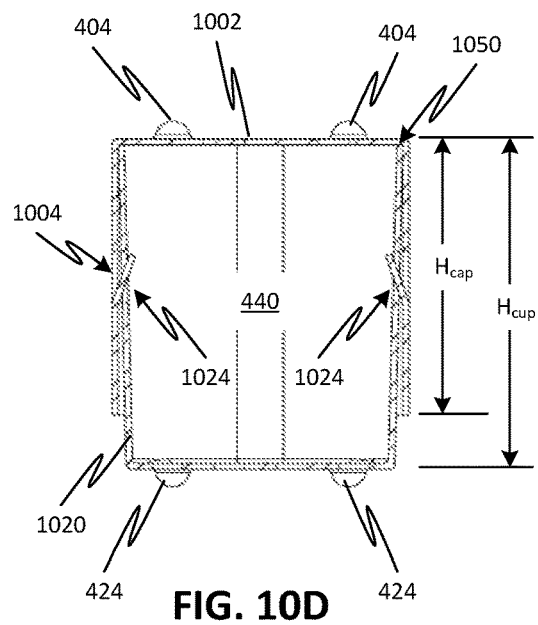
FIG. 10D
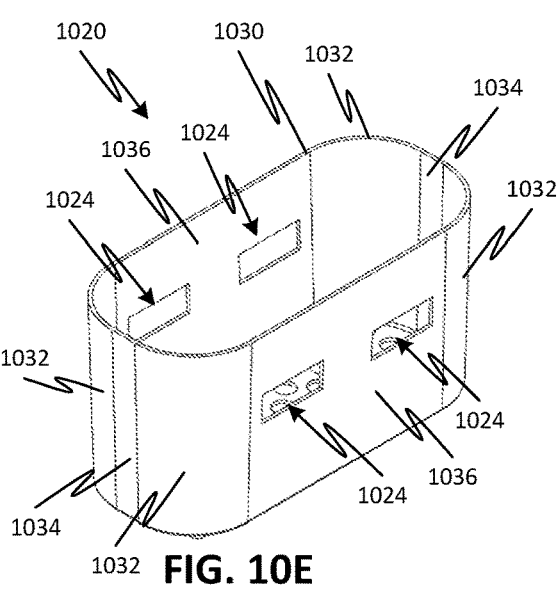
FIG. 10E

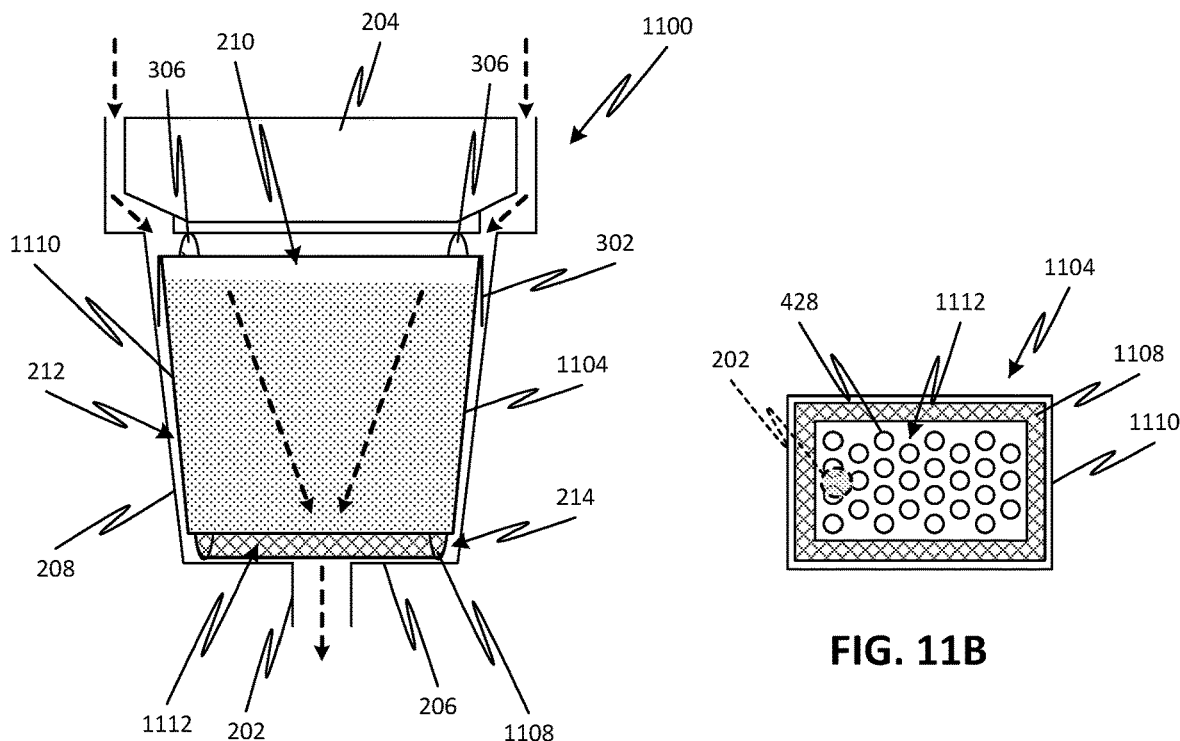
FIG. 11A
FIG. 11B
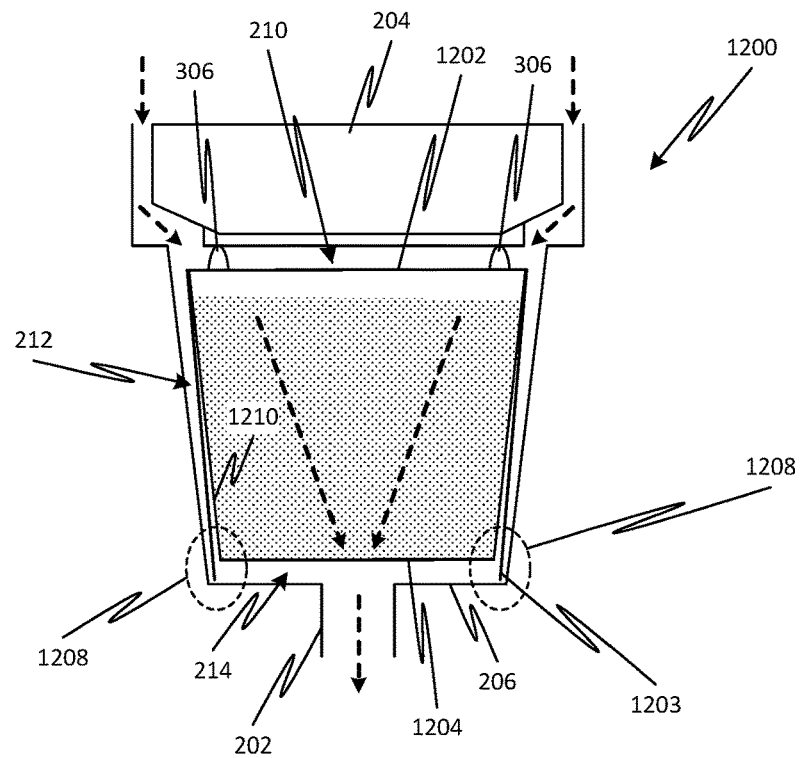
FIG. 12

CAPSULES FOR USE IN PERSONAL VAPORIZERS

CROSS-REFERENCE TO RELATED APPLICATIONS

The present application claims the benefit of U.S. Provisional Application No. 62/685,543, filed Jun. 15, 2018, which is hereby incorporated by reference herein in its entirety.

FIELD

The present disclosure relates generally to vaporization devices, and more particularly, to capsules for holding a vaporizable material for use in portable/personal electronic vaporization devices.

BACKGROUND

A user of a portable/personal electronic vaporization device loads a material to be vaporized (or aerosolized) into the vaporization device, for example, by removing a lid, filling a vaporization chamber of the oven (heating chamber) with the material, and replacing the lid. The vaporization device heats the loaded material to a predefined temperature that generates the desired vapors. The user inhales the vapors by sucking at an inlet end of the vaporization device, which pulls air through the vaporization chamber. The lid is constructed to cover an opening of the vaporization chamber while allowing air external to the vaporization device to pass around the lid to enter the vaporization chamber. For example, the vaporization device can be a PAX 2 or PAX 3 vaporizer (PAX Labs, Inc.).

Direct loading of the vaporizable material into the vaporization chamber causes fouling of the oven, thereby requiring frequent cleaning. Failure to clean the oven can lead to reduced operating efficiency or overheating of the vaporization device. To address this issue, the inventors have studied a capsule that can be filled with the material to be vaporized and then loaded into the vaporization chamber. For example, FIGS. 1A-1B diagrammatically illustrate such a capsule 100, which includes a cap 102 and a cup 104. The cap 102 is coupled to the cup 104 so as to enclose an interior volume 106 that holds the vaporizable material 108, as shown in FIG. 1B. The cap 102 is held to the cup 104 by press-fit interaction between a lip of the cup 104 and an inner wall of the cap 102, as illustrated at 110. Top and bottom surfaces of the cap 102 and the cup 104 have holes (not shown) therein that allow air to pass into and out of the interior volume 106. After use, the capsule can be removed and replaced by another loaded capsule. The removed capsule can be discarded (i.e., one-time use capsule), or opened, cleaned, and re-loaded (i.e., multi-use capsules). In either case, the frequency and/or intensity of oven cleaning can be reduced.

The present inventors have found that such a capsule 100 may interact with the oven and/or the lid to reduce air flow through the interior volume 106, thereby impairing performance of the vaporization device. FIG. 2A shows the capsule 100 loaded within an oven 200 of a vaporization device in an inverted orientation, i.e., where gravity is in a direction from lid 204 toward bottom wall 206 of the oven 200. The oven 200 has an outlet 202 at bottom wall 206, and a tapered sidewall 208 extending from the bottom wall 206 to an upper inlet portion. A lid 204 sits within the upper inlet portion of the oven 208, thereby retaining the capsule 100 within the vaporization chamber while allowing air (dashed lines) to enter the vaporization chamber from outside the vaporization device when a vacuum (e.g., suction by a user) is applied to outlet 202.

In the orientation of FIG. 2A, the capsule 200 falls to the bottom of the oven 200 due to the effect of gravity, with the bottom surface of the cup 104 resting on the bottom wall 206 of the oven 200. Thus, there is no (or a minimal) gap 214 between the bottom wall 206 and the capsule 100, such that air flow through holes in the bottom of cup 104 may be blocked or impeded. As a result, it may be difficult to draw air through the interior volume of the capsule 100.

FIG. 2B shows an opposite orientation to that of FIG. 2A, i.e., where gravity is in a direction from the bottom wall 206 of the oven 200 toward lid 204. In this orientation, gravity causes the capsule 100 to fall to the inlet portion of the oven 200, thereby resting on the lid 204. Thus, there is no (or a minimal) gap 210 between the lid 204 and the capsule 100, such that air flow through holes in the cap 102 may be blocked or impeded. Moreover, the shape of the capsule 100 does not closely follow the profile of the oven 200, such that a substantial gap 212 between oven sidewall 208 and the capsule 100 exists. As a result, air may preferentially flow from the inlet portion adjacent the lid 204 to outlet 202 via gap 212 rather than through the interior volume of the capsule 100.

In intermediate orientations (i.e., an orientation between those illustrated in FIGS. 2A-2B), the substantial sidewall gap 212 and the reduced gaps 210, 214 at the top and bottom of the capsule may cooperate to impede air flow through the capsule and/or cause air to bypass the capsule en route to the outlet 202. For example, in an intermediate orientation, the capsule 100 may be tilted within the vaporization chamber of the oven 200, thereby encouraging air to bypass the capsule 100 via gaps 210, 212, and 214.

The present invention has been devised based on the inventors' study, with a view toward providing a capsule that ensures excellent performance of the vaporization device, and thus a satisfying user experience.

SUMMARY

In embodiments, capsules are provided with standoff structures that position the respective capsule to avoid occlusion of its air inlet/outlet holes by surfaces of the oven and/or lid that form a vaporization chamber of the personal vaporization device. Moreover, during use of the vaporization device, the capsule design encourages air to flow through the material held within the capsule via the air inlet/outlet holes, rather than flowing around the capsule to bypass the vaporizable material held therein. In some embodiments, the capsules include tamper-resistant features that inhibit disassembly of the capsule, thereby preventing access to vaporizable material held within the capsule. In some embodiments, a kit comprises separate pieces that can be coupled together to assemble the capsule.

In one or more embodiments, a capsule for use in a personal vaporization device comprises a cap, a cup, and first and second standoff structures. The cap has a first base wall with a plurality of holes extending through the first base wall, and a first peripheral skirt extending from the first base wall. The cup has a second base wall with a plurality of holes extending through the second base wall, and a first peripheral sidewall extending from the second base wall. The first standoff structure is on a side of the first base wall opposite the first peripheral skirt, and the second standoff structure is on a side of the second base wall opposite the first peripheral sidewall. The cap and the cup are coupled together and enclose an interior volume for holding a vaporizable material between the first base wall and the second base wall. The first and second standoff structures are constructed to space the first base wall and the second base wall, respectively, from adjacent surfaces of the personal vaporization device.

In one or more embodiments, a capsule for use in a personal vaporization device comprises means for spacing opposing base walls of the capsule from respective facing portions of the personal vaporization device. The opposing base walls each have a plurality of air-transfer through-holes therein.

In one or more embodiments, a vaporization system comprises an oven, a lid, and the inventive capsule disposed in a vaporization chamber formed by the oven and the lid.

Objects and advantages of embodiments of the disclosed subject matter will become apparent from the following description when considered in conjunction with the accompanying drawings.

BRIEF DESCRIPTION OF DRAWINGS

Embodiments of the invention will hereinafter be described with reference to the accompanying drawings, which have not necessarily been drawn to scale. Where applicable, some elements may be simplified, have dimensions exaggerated, or otherwise not illustrated in order to assist in the illustration and description of underlying features. Throughout the figures, like reference numerals denote like elements.

FIG. 10A is an isometric view of a capsule according to a second variation of the second embodiment.

FIGS. 10B-10C are cross-sectional and isometric views of a cap of the capsule of FIG. 10A.

FIG. 10D is a cross-sectional view of the capsule of FIG. 10A, showing the tamper-resistant interaction between the cap and the cup.

FIG. 10E is an isometric view of the cup of the capsule of FIG. 10A.

FIG. 11A is an explanatory diagram of a capsule according to a second variation of the first embodiment in an oven of a personal vaporization device.

FIG. 11B is a bottom view of the capsule of FIG. 11A.

FIG. 12 is an explanatory diagram of a capsule according to a third variation of the first embodiment in an oven of a personal vaporization device.

DETAILED DESCRIPTION

The terms "horizontal" and "vertical" have been used herein to describe the relative locations of different components of the disclosed embodiments. However, the embodiments are not limited to strictly horizontal and vertical directions. Where such descriptive terms are used, they are to include deviations therefrom. For example, "horizontal" can include directions that have a minor vertical component (e.g., up to 10%) and "vertical" can include directions that have a minor horizontal component (e.g., up to 10%).

Moreover, the terms "top," "bottom," "side," "horizontal," and "vertical" have been used herein for convenience to described relative orientations of components and are not intended to limit an arrangement of the capsule or oven with respect to gravity. Indeed, it is contemplated that in some embodiments of the disclosed subject matter, the vertical direction may extend perpendicular to the direction of gravity and the horizontal direction may extend parallel to the direction of gravity.

In this application, unless specifically stated otherwise, the use of the singular includes the plural and the use of "or" means "and/or." Furthermore, use of the terms "including" or "having," as well as other forms, such as "includes," "included," "has," or "had" is not limiting. Any range described herein will be understood to include the endpoints and all values between the endpoints.

In embodiments of the disclosed subject matter, a capsule for use in a personal vaporization device has top and bottom standoff structures, which keep respective vented surfaces of the capsule at a set spacing from facing structures of the vaporization device, thereby preventing blockage of the holes of the capsule. In addition, components of the capsule can be sized and shaped to closely follow the profile of the oven, thereby minimizing (and preferably eliminating) a gap between the oven sidewalls and a periphery of the capsule. When fully installed in the oven, the cap of the capsule will preferably have a sliding fit with the oven wall, or at least a minimized gap between the cap and the oven wall. As a result, air can more reliably flow through the capsule, and airflow bypassing the capsule to the oven outlet can be avoided.

In additional embodiments, components of the capsule can include tamper-resistant features that prevent (or at least inhibit) separation of the components (e.g., to access the interior volume of the capsule) without otherwise destroying the capsule, or at least rendering it unsuitable for subsequent use in the vaporization device. A supplier can thus fill and assemble the capsule to have at a predetermined dosage without fear of subsequent alteration by an end user or an intermediary.

Figure 3A:
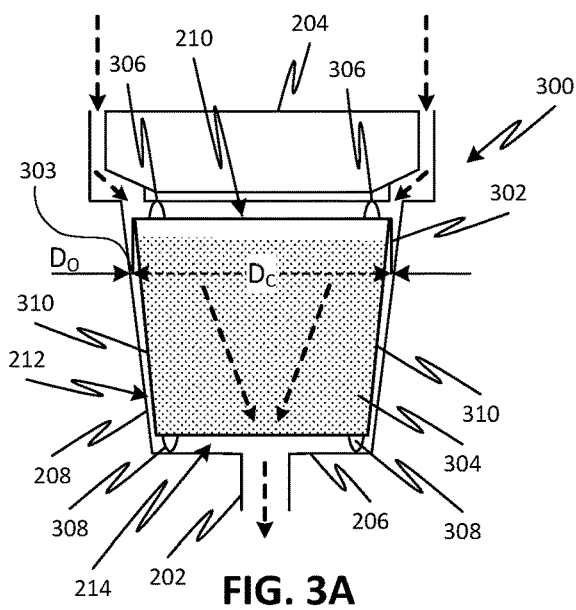
FIG. 3A is an explanatory diagram of a capsule according to a first embodiment in an oven of a personal vaporization device.

In a first embodiment, a capsule 300 includes standoff structures 306, 308, as illustrated in FIG. 3A. For example, cap 302 of the capsule 300 has a standoff structure 306 projecting from an upper surface thereof, while cup 304 has a standoff structure 308 projecting from a lower surface thereof. When loaded into the oven 200, the standoff structure 306 of the cap 302 abuts the lid 204 to maintain a minimum offset for the spacing 210 between the lid 204 and the vented surface of the cap 302. Similarly, the standoff structure 308 of the cup 304 abuts the bottom wall 206 of the oven to maintain a minimum offset for the spacing 214 between the oven 200 and the vented surface of the cup 304. As a result, the vented surfaces of cap 302 and cup 304 can remain unblocked by facing surfaces of the vaporization chamber. Moreover, by appropriately sizing the standoff structures, a position of cup 304 between lid 204 and bottom wall 206 of oven 200 can be stabilized.

In the illustrated embodiment, each standoff structure 306, 308 includes one or more feet (e.g., stamped protrusions) extending from respective vented surfaces of the cap 302 and the cup 304. The feet are disposed at locations at a periphery of the respective vented surface and can be arranged to prevent tilting of the capsule 300 or lid 204 during loading or changes in orientation of the vaporization device, while avoiding disruption to air flow into the capsule. For example, each vented surface has four feet, each disposed at a respective corner of the vented surface (for example, as illustrated in FIGS. 4A-4G).

Figure 3B:
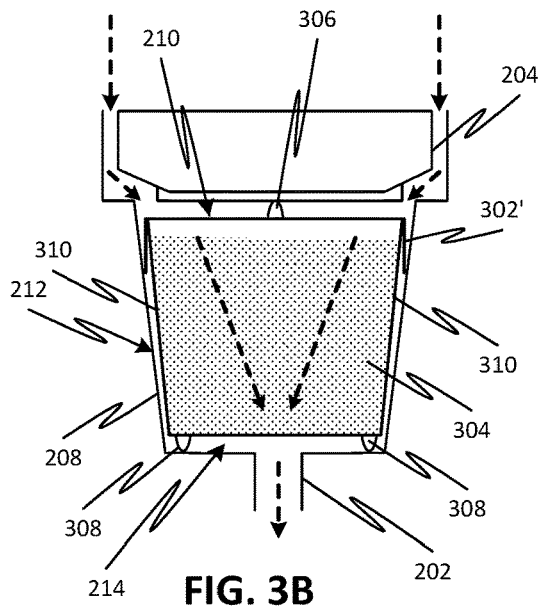
FIG. 3B is an explanatory diagram of a capsule according to a first variation of the first embodiment in an oven of a personal vaporization device.

Other arrangements and number of feet are also possible according to one or more contemplated embodiments. For example, FIG. 3B shows a variation where cap 302' includes a single foot 306 at a center of its vented surface, while the cup 304 retains a set of four feet 308 at respective corners of its vented surface. In such a configuration, the single foot 306 may provide less of an obstruction to the inlet flow from the lid 204 into the capsule; however, the capsule and lid 204 may also be susceptible to positional misalignment during loading or changes in vaporization device orientation.

Returning to FIG. 3A, the cap 302 can be sized and shaped so as to form a sliding fit with the sidewall 208 of the oven 200 over at least a portion of the cap's height. In particular, at least the bottom edge 303 of the skirt of the cap 302 (opposite the standoff structure 306 in a height direction of the cap 302) contacts the oven sidewall 208, thereby forming a seal that prevents (or at least discourages) air from flowing into gap 212. Due to manufacturing tolerances and other variations in oven geometry, there may nevertheless be a slight gap between the cap 302 and the oven sidewall 208. However, the dimensions of the cap 302 are chosen to minimize a gap between the cap 302 of the inserted capsule and the closest portion of the oven sidewall 208. Preferably, for a given exterior cross-dimension Dc of the bottom edge 303 of the skirt of the cap 302 (length or width), the corresponding cross-dimension Do of the opening defined by the oven sidewall 208 at a height of the bottom edge 303 of the cap 302 of the inserted capsule is no more than 0.5 mm. Accordingly, the cap 302 may more broadly be considered to make a substantially sliding fit with the oven sidewall 208, wherein the term substantially sliding fit is defined as including an actual sliding fit as well as a fit within the aforementioned 0.5 mm cross-dimensional tolerance.

Figure 1A:
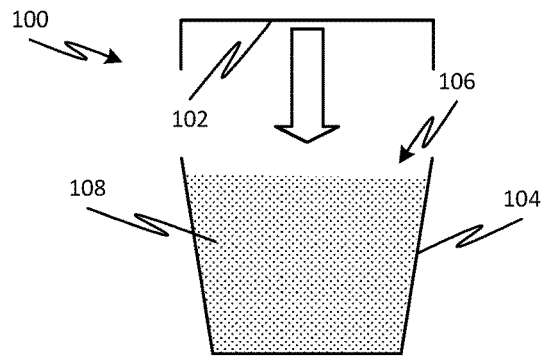
FIGS. 1A-1B are explanatory diagrams of a capsule according to a comparative example, prior to assembly and after assembly, respectively.
Figure 1B:
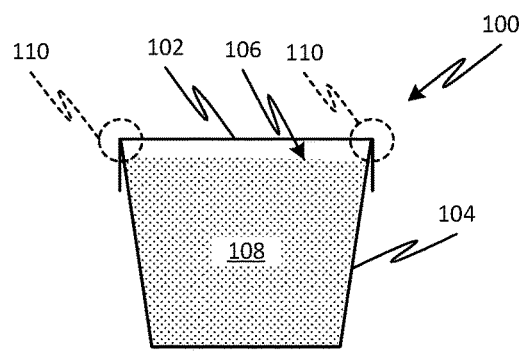
Figure 2A:
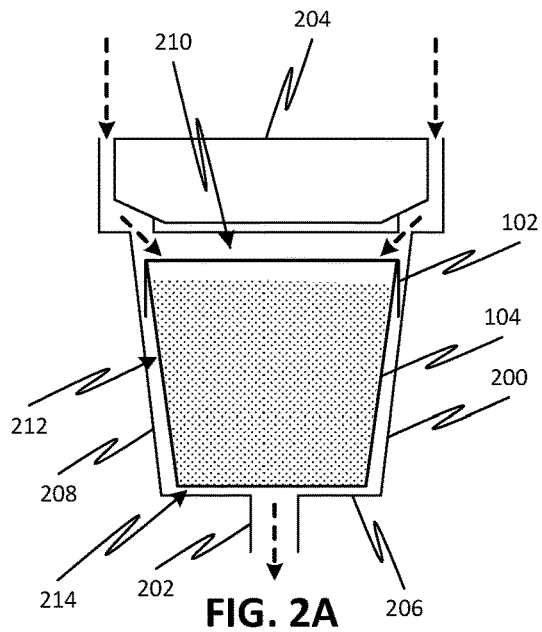
FIGS. 2A-2B are explanatory diagrams of the capsule of FIG. 1B in an oven of a personal vaporization device.
Figure 2B:
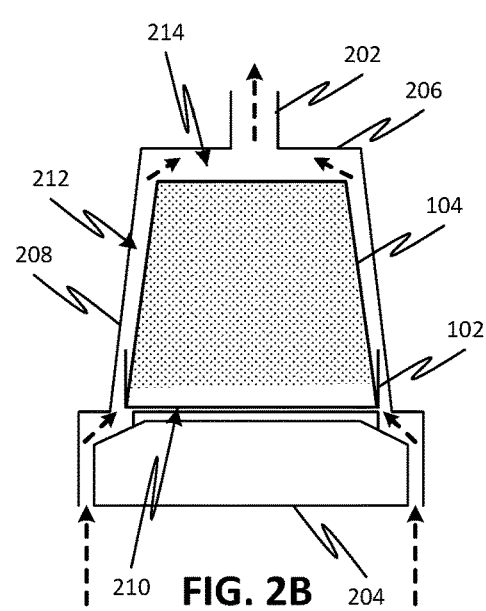

In addition, at least the cup 304 of the capsule 300 has a sidewall 310 that is sized and shaped to closely follow the profile of the sidewall 208 of the oven 200. For example, where a sidewall 208 of the oven 200 is tapered at a particular draft angle, the sidewall 310 of the cup 304 is tapered at the same draft angle, while the skirt of the cap 302 may be substantially straight (not tapered). The gap 212 between the oven sidewall 208 and capsule 300 may thus be minimized, or at least reduced as compared to the configurations of FIGS. 2A-2B. The reduced gap 212 presents a less favorable air flow path such that air is encouraged to flow through the capsule 300. The sliding fit of the cap 302 in combination with the reduced gap 212 can force more air to flow through the interior volume of the capsule 300 en route to outlet 200 rather than bypassing the capsule 300. Preferably at least 80% of the air, more preferably at least 90% of the air, and more preferably substantially 100% of the air is forced to flow through the capsule 300.

FIGS. 4A-7E show various views of an exemplary capsule 400 and oven 500 assembly according to the first embodiment. Capsule 400 includes a cap 402 and a cup 420 that fit together to form an enclosed interior volume 440. The cap 402 has a vented surface 406 (first base wall) with a plurality of holes 408 extending therethrough and feet 404 (protrusions) at corners of the vented surface 406. Similarly, the cup 420 has a vented surface 426 (second base wall) with a plurality of holes 428 extending therethrough and feet 424 (protrusions) at corners of the vented surface 426. For example, each foot 404, 424 is a protrusion or protuberance formed in the respective vented surface 406, 426 by stamping. In such a fabrication or otherwise, each foot 404, 424 has a rounded portion 405, 425 (radiused portion) adjacent to the respective surface 406, 426, which rounded portions may help in maintaining a constant wall thickness during formation of the feet.

Depending from a periphery of the vented surface 406 is a vertically extending sidewall 410 (peripheral skirt) that defines a first recess 448. Similarly, the cup 420 has a vertically extending sidewall 430 (peripheral sidewall) that extends from a periphery of the vented surface 426 and defines a second recess 440. The cap sidewall 410 is constructed to overlap with a sidewall 430 of the cup 404 along region 442. For example, the cap 402 is designed to form a press fit with lip 444 at a top of the cup sidewall 430 when the cup 420 is fully inserted into recess 448 of the cap 402.

Figure 7A:
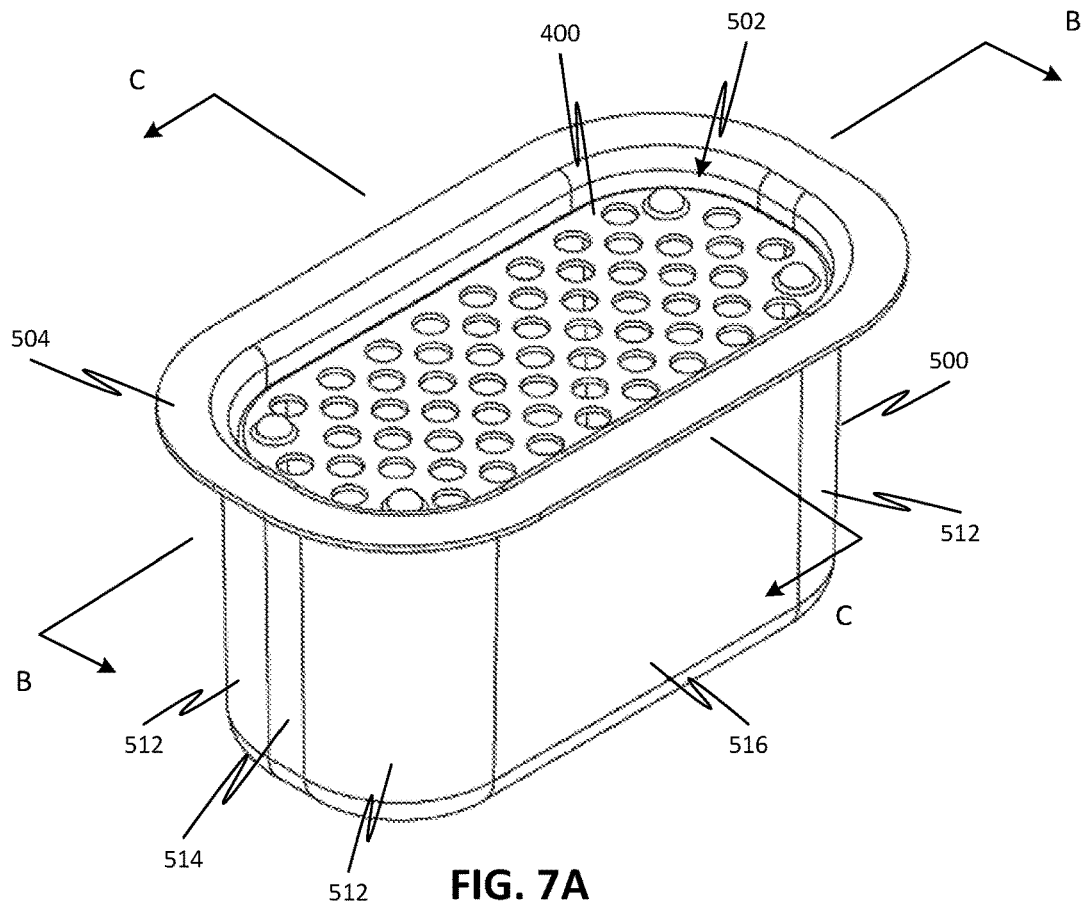
FIG. 7A is an isometric view of the capsule according to the first embodiment within an oven of an electronic vaporization device.

The cap 402 has a shape in top-down plan view (e.g., FIGS. 4B and 6B) similar to that of oven 500. For example, the sidewall 410 has substantially flat portions 414 and 416 connected together by intervening curved portions 412. Similarly, cup 420 has a shape in top-down plan view (e.g., FIG. 5B) similar to that of oven 500. For example, sidewall 430 has substantially flat portions 434 and 436 connected together by intervening curved portions 432. As a result, capsule 400 may better conform to sidewalls 508 of oven 500, which has flat portions 514 and 516 connected together by intervening curved portions 512 (FIG. 7A).

Figure 4A:
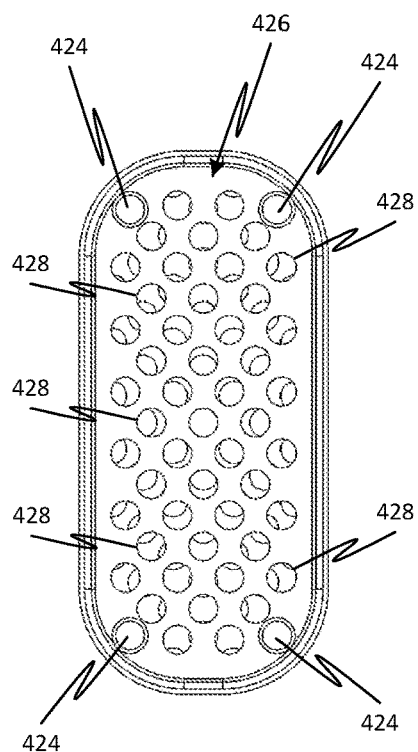
FIGS. 4A-4C are bottom, top, and isometric views of a capsule according to the first embodiment.
Figure 4B:
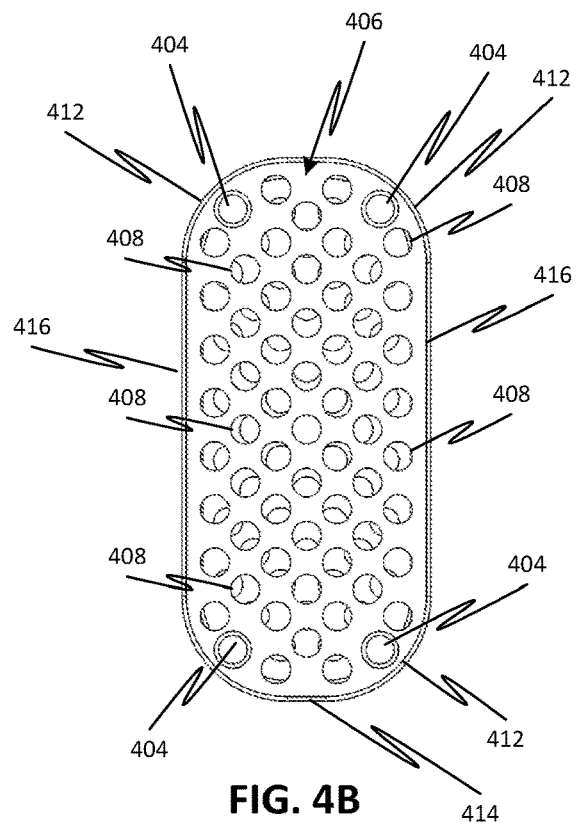
Figure 4C:
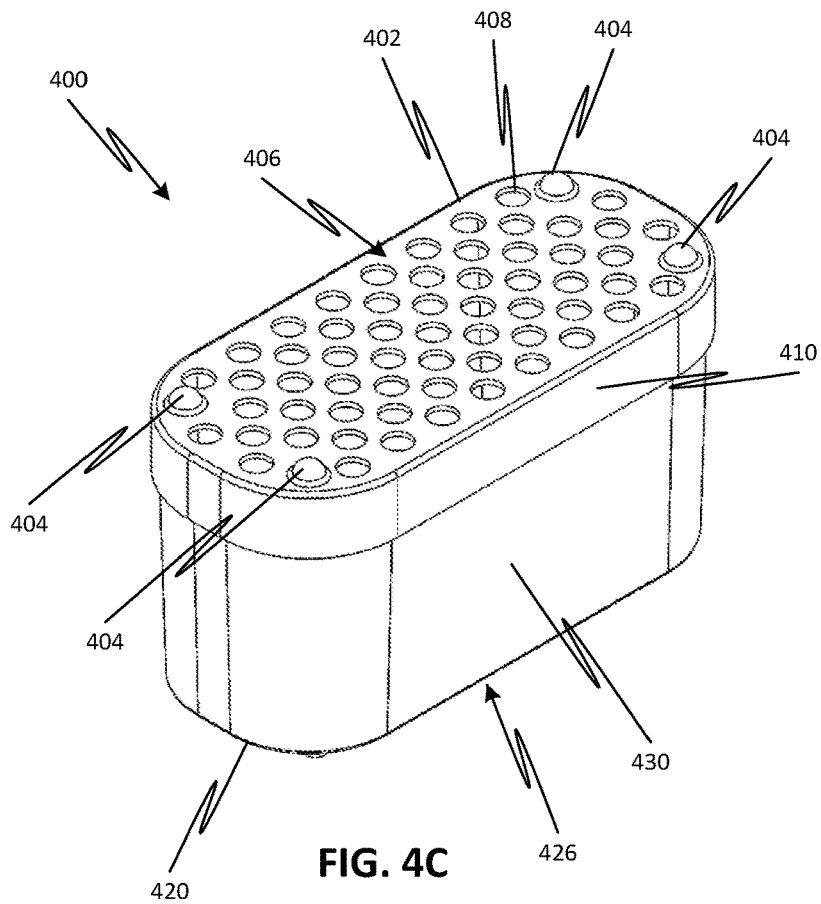
Figure 4D:
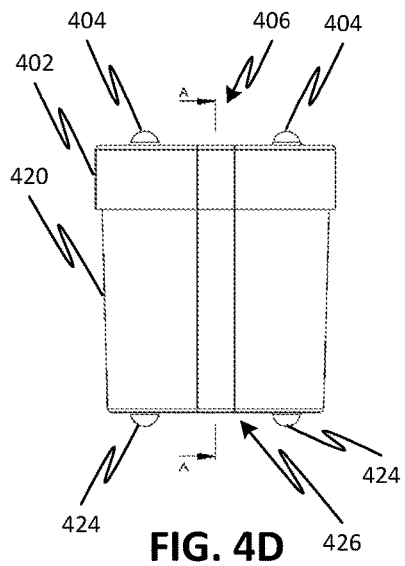
FIGS. 4D and 4F are end and side views, respectively, of the capsule according to the first embodiment.
Figure 4E:
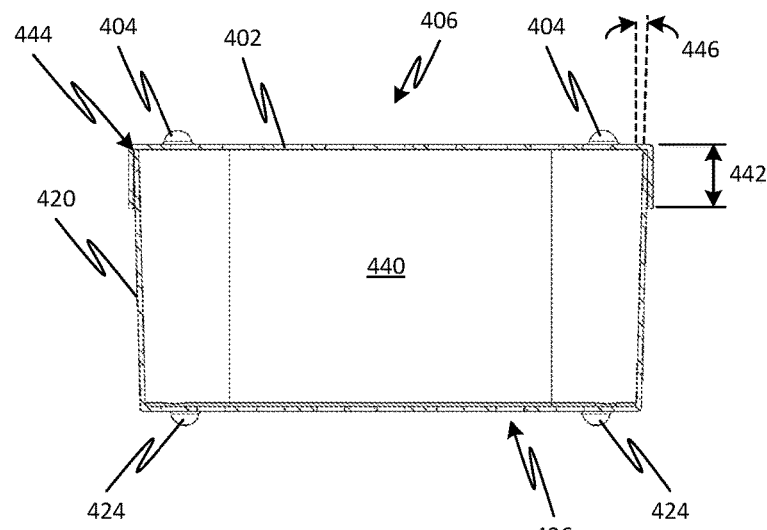
FIGS. 4E and 4G are cross-sectional views of A-A in FIG. 4D and B-B in FIG. 4F, respectively, for the capsule according to the first embodiment.
Figure 4F:
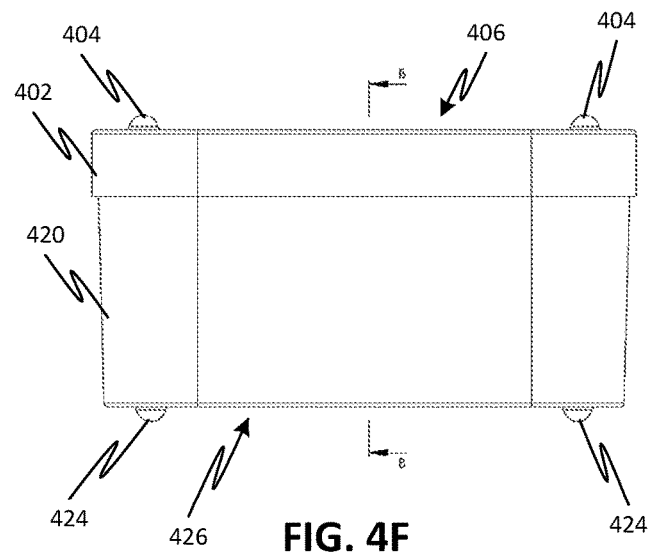
Figure 4G:
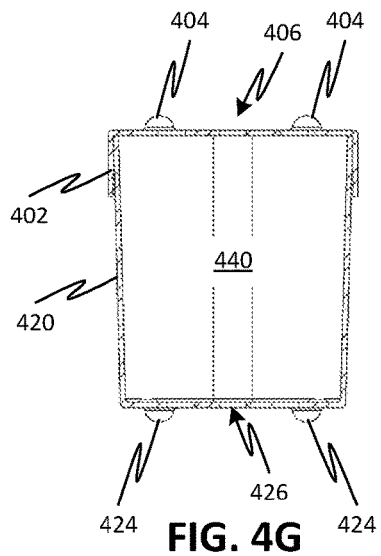
Figure 5A:
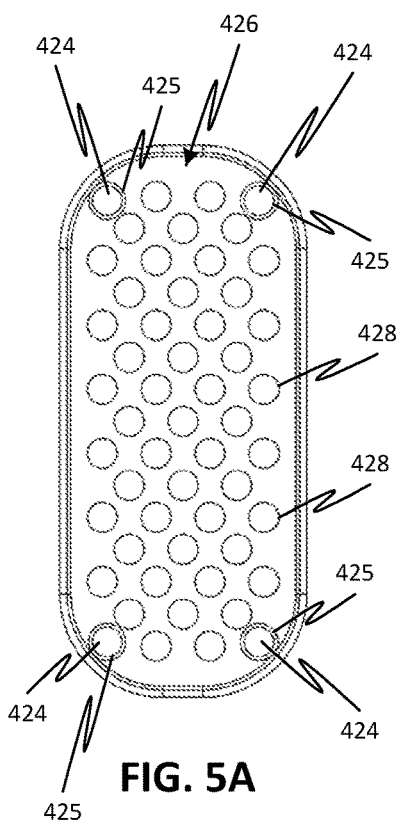
FIGS. 5A-5C are bottom, top, and isometric views of a cup component of the capsule according to the first embodiment.
Figure 5B:
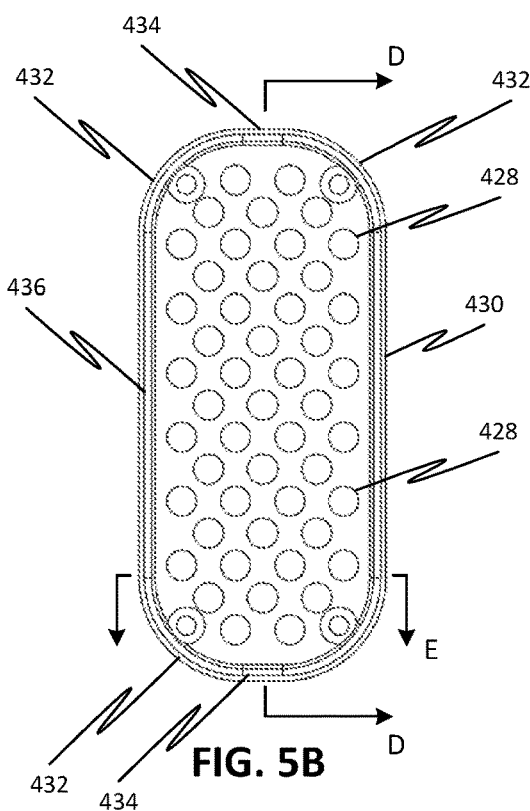
Figure 5C:
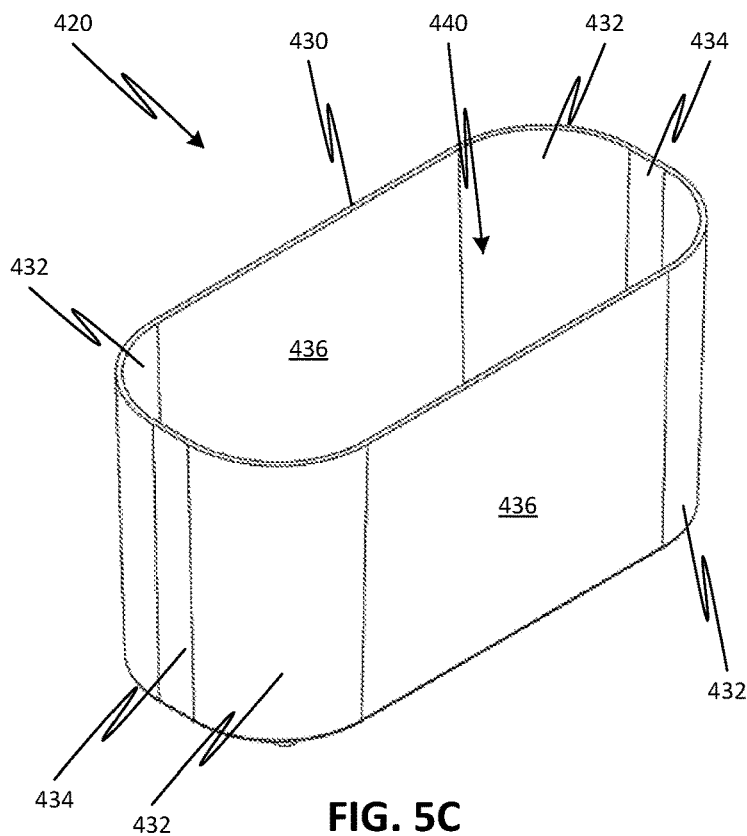
Figure 5D:
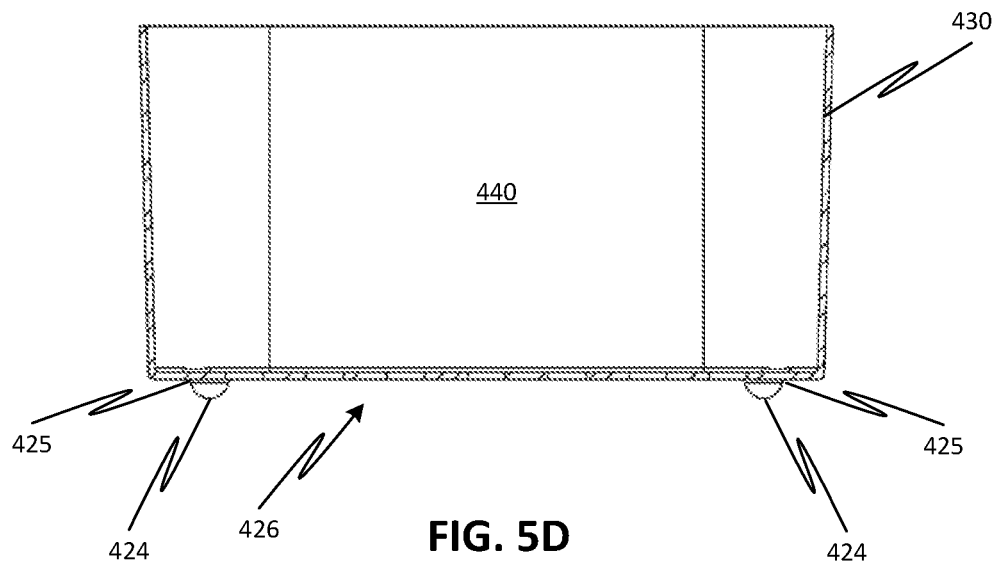
FIGS. 5D-5E are cross-sectional views of D-D and E-E in FIG. 5B, respectively, for the cup component of the capsule according to the first embodiment.
Figure 5E:
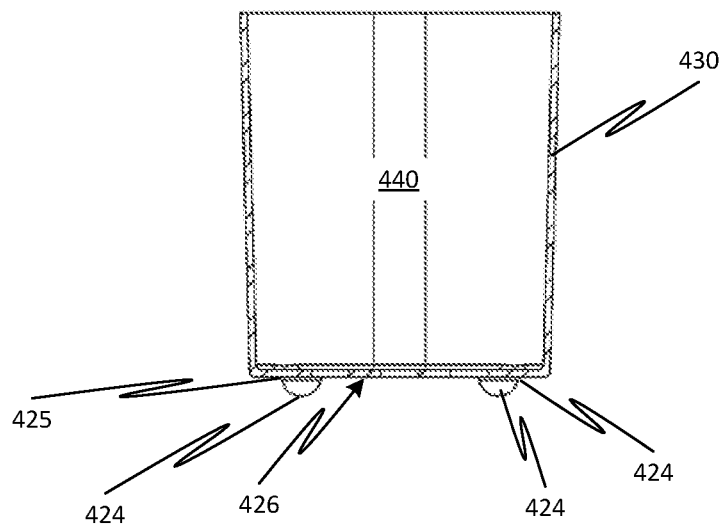
Figure 6A:
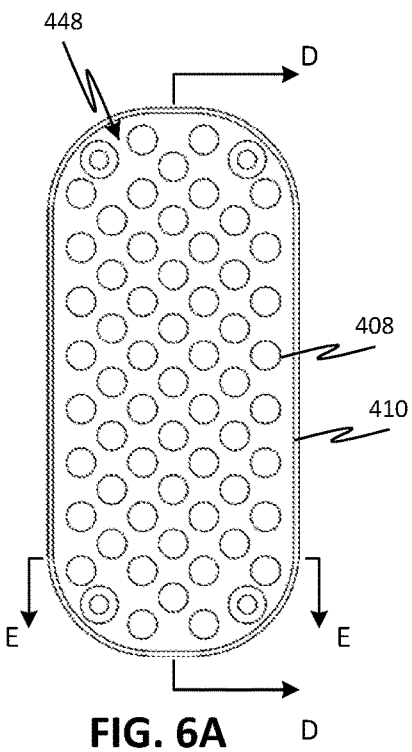
FIGS. 6A-6C are bottom, top, and isometric views of a cap component of the capsule according to the first embodiment.
Figure 6B:
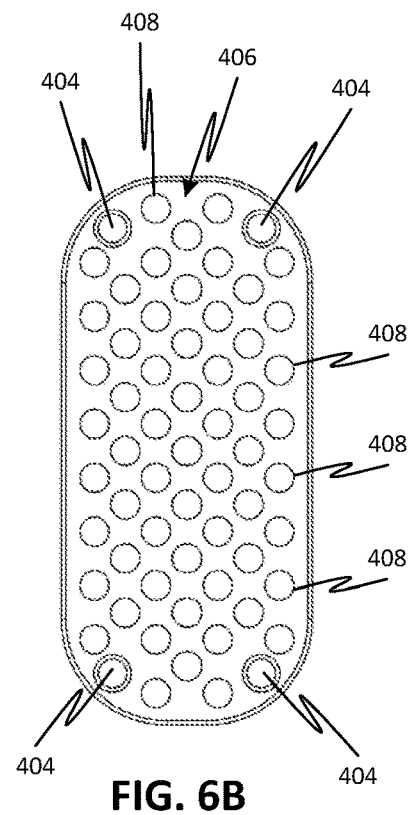
Figure 6C:
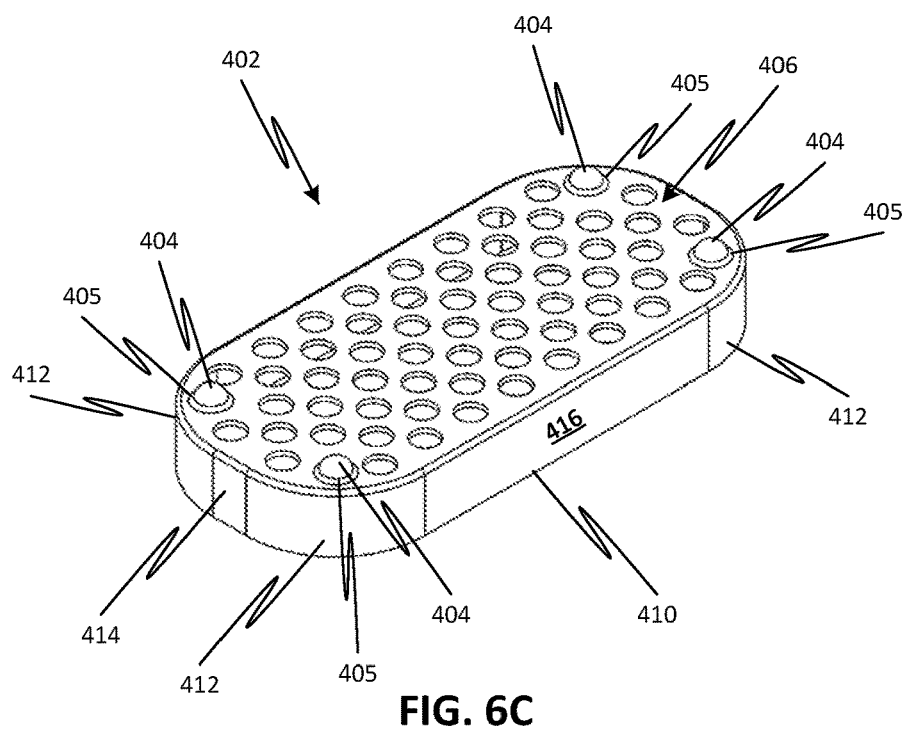
Figure 6D:
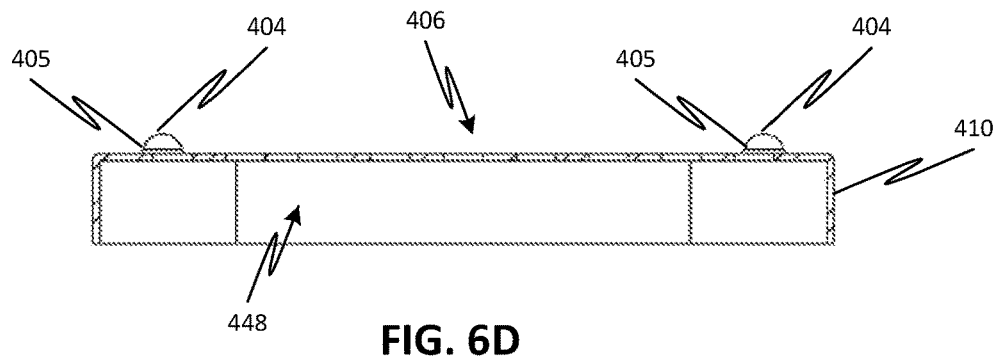
FIGS. 6D-6E are cross-sectional views of D-D and E-E in FIG. 6A, respectively, for the cap component of the capsule according to the first embodiment.
Figure 6E:
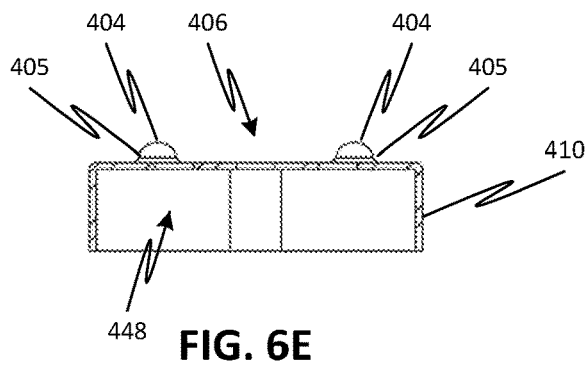
Figure 7B:
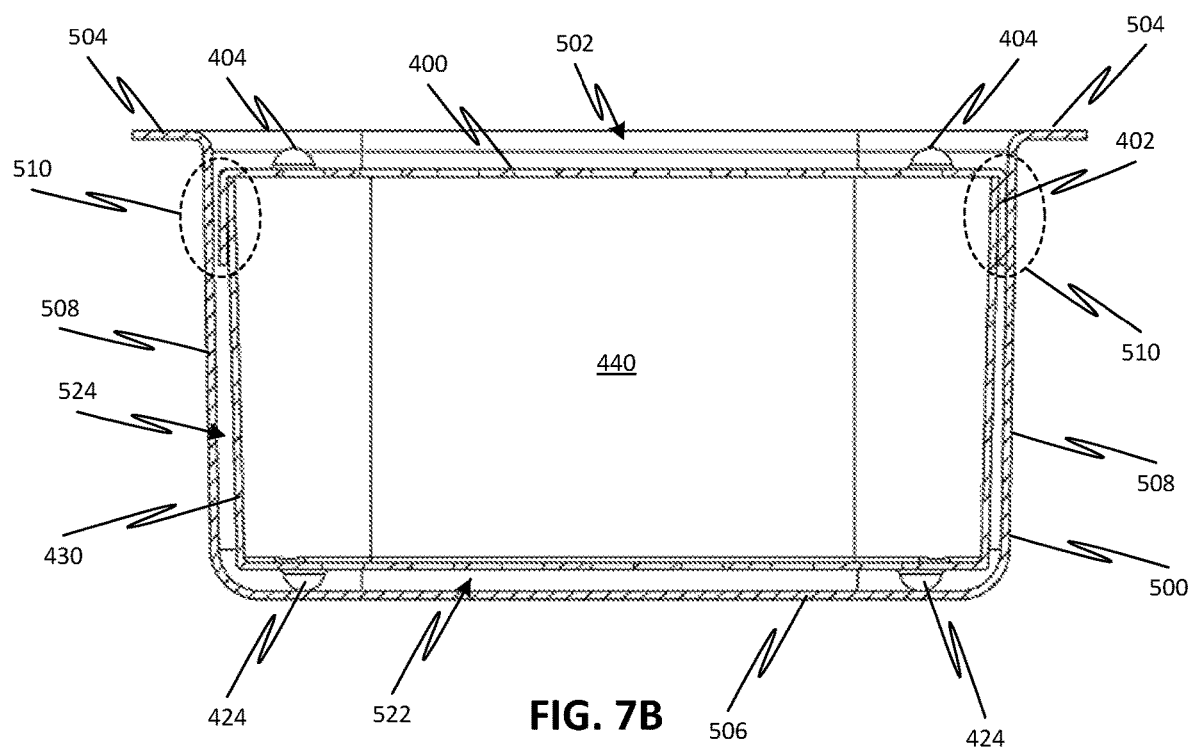
FIGS. 7B-7C are cross-sectional views of B-B and C-C in FIG. 7A, respectively.
Figure 7C:
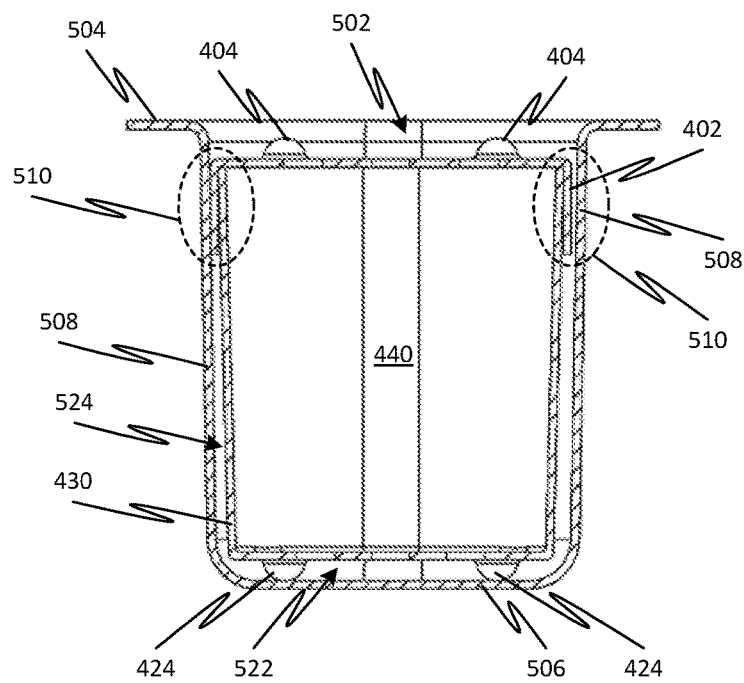

In addition, sidewalls 430 of the cup 420 follows a profile of sidewalls 508 of the oven 500 in cross-sectional view, so as to minimize (or at least reduce) the gap 524 between oven sidewall 508 and cup sidewall 430 (FIGS. 7B-7C). For example, as illustrated in FIG. 4E, the cup sidewalls 430 may be tapered, i.e., having a non-zero angle 446 with respect to vertical (i.e., perpendicular to the vented surface 426). As such, a planar area of the vented surface 406 of the cap 402 may be larger than that of the vented surface 426 of the cup 420.

Figure 7D:
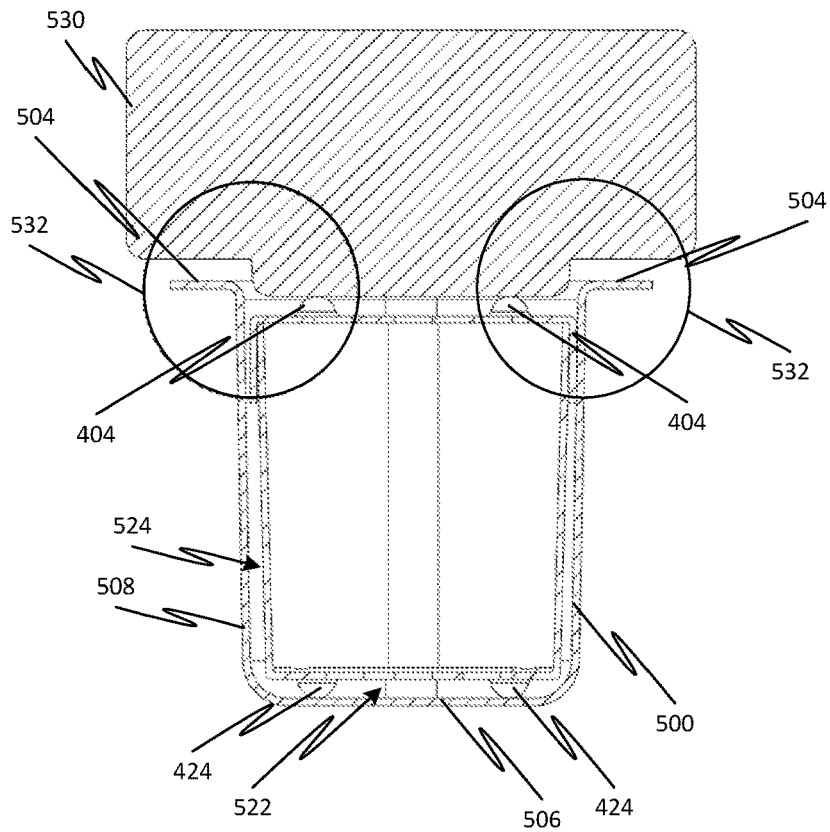
FIGS. 7D-7E are cross-sectional views similar to FIGS. 7C and 7B, respectively, with a lid 530 of the vaporization device in place.
Figure 7E:
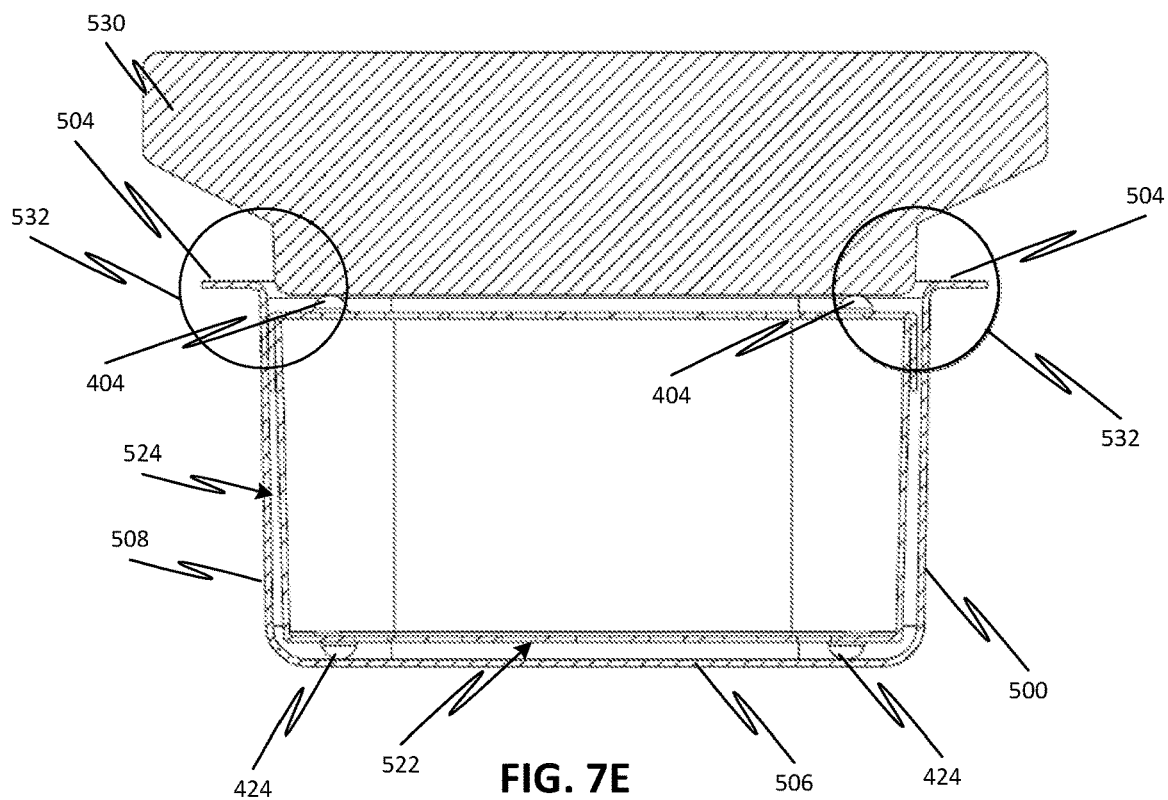

Since the cap sidewall 410 is disposed outside a periphery of the cup sidewall 430, the cap 402 makes a substantially sliding fit with the oven sidewall 508 in region 510 proximal to the air inlet (i.e., when lid 530 is installed in inlet region 502 of oven 500, the inlet would be defined between the lid 530 and annular flange 504 of the oven 500, for example, in regions 532 in FIGS. 7D-7E), which may encourage air to flow through the vented surface 406 of cap 402 rather than through gap 524 between oven sidewall 508 and cup sidewall 430. Moreover, the shape and taper of the sidewall 430 can reduce the size of gap 524, thereby further encouraging air to flow through the capsule 400 rather than around capsule 400. Meanwhile, the cap feet 404 and the cup feet 424 act to define minimum spacings for a gap between the lid 530 and the capsule 400 at the inlet 502 and a gap 522 between a bottom surface 506 and the capsule 400, so as to prevent (or at least reduce) occlusion of holes 408, 428. Air flow through the capsule 400 can thus be improved.

Although feet (e.g., stamped protrusions) have been illustrated for the standoff structures of the capsule described above, embodiments of the disclosed subject matter are not limited thereto. For example, in a first variation of the first embodiment, the feet 308 on the bottom of cup 304 of capsule 300 in FIG. 3A can be replaced with a continuous annular rib 1108 (e.g., stamped protrusion) on the bottom of cup 1104 of capsule 1100, as illustrated in FIGS. 11A and 11B. The rib 1108 thus forms an enclosed region 1112 overlapping with the outlet 202, which may advantageously interact with oven bottom wall 206 to isolate gap 212 between cup sidewall 1110 and oven sidewall 208 from outlet 202, and thereby encourage air to flow through the interior of the capsule 1100 en route to outlet 202. Although outlet 202 is shown in FIG. 11B as being surrounded by rib 1108, it is also possible for the outlet 202 to partially overlap with rib 1108, so long as the outlet 202 does not extend outside rib 1108 to communicate with gap 212.

In a second variation of the first embodiment, the rib 1108 on the bottom of cup 1104 of capsule 1100 in FIG. 11A is replaced with a portion of the cap that protrudes past a bottom of the cup to achieve the same effect. In particular, FIG. 12 illustrates a capsule 1200 where its cap 1202 has a vertically extending sidewall 1203 (peripheral skirt) that has a height greater than the vertically extending sidewall 1210 (peripheral sidewall) of the cup, such that the cap sidewall 1203 extends beyond the cup bottom wall 1204 when the cup is fully inserted into the cap. As a result, the extending portion of the cap sidewall 1203 acts as a rib in region 1208 to offset the cup bottom wall 1204 from the oven bottom surface 206, similar to the arrangement of FIGS. 11A-11B. The disposition of the cup fully within the cap 1202 may also offer some measure of tamper resistance by making it difficult for an end user to access the interior of the capsule 1200 once the cup is fully inserted into the cap.

Aspects of second embodiments will now be described with respect to FIGS. 8A-10E. In many respects, features of the second embodiment (e.g., standoffs, vented surfaces, surfaces conforming to the oven) can be the same as the first embodiment and thus will not be repeated in detail below. In addition to features of the first embodiment, however, the second embodiment includes tamper-resistant features that prevent (or at least resist) separation of the cap and the cup after loading and assembly of the capsule.

Figure 8A:
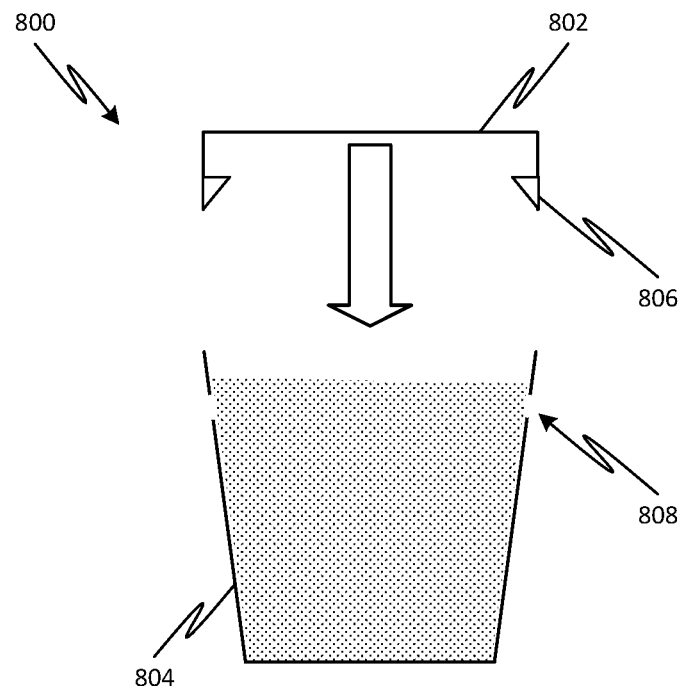
FIGS. 8A-8B are explanatory diagrams of a capsule according to the second embodiment, prior to assembly and after assembly, respectively.
Figure 8B:
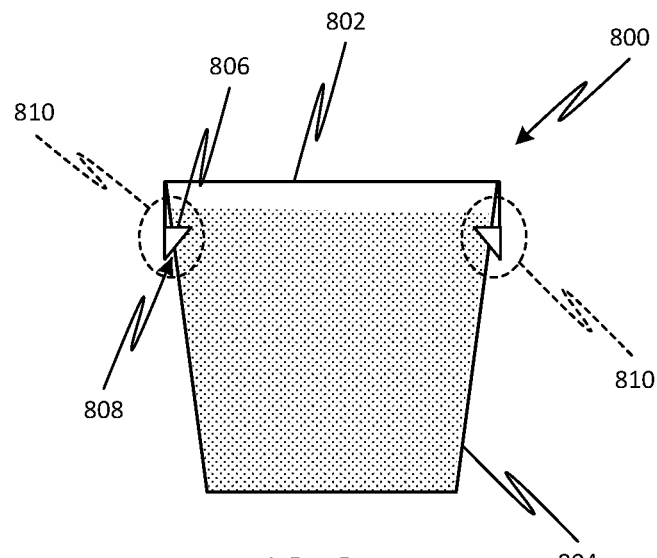

In a second embodiment, cap 802 and cup 804 of capsule 800 are provided with cooperating features on respective sidewalls thereof that engage with each other during assembly, as illustrated in FIGS. 8A-8B. For example, cap 802 can have one or more protrusions 806 that are designed to fit into or otherwise engage with one or more sidewall receptacles 808 of cup 804, as shown at 810. After assembly, it becomes difficult or impossible to remove protrusions 806 from receptacles 808 without otherwise destroying or damaging the capsule 800, thereby rendering it unsuitable for reuse.

FIGS. 9A-9E show various views of an exemplary capsule 900 according to a first variation of the second embodiment. Capsule 900 includes a cap 902 and a cup 920 that fit together to form an enclosed interior volume 440. Depending from a periphery of the vented surface of the cap 902 is a vertically extending sidewall 910 (peripheral skirt), which has substantially flat portions 914 and 916 connected together by intervening curved portions 912. Along at least one of the flat portions, e.g., longer flat portions 916, is formed a pair of inwardly extending protrusions 904. For example, each protrusion 904 can be formed in the respective flat portion 916 by stamping. In such a fabrication or otherwise, each protrusion 904 can have a rounded portion 905 (radiused portion) adjacent to respective surface 916, which rounded portions may help in maintaining a constant wall thickness during formation of the protrusions.

Figure 9A:
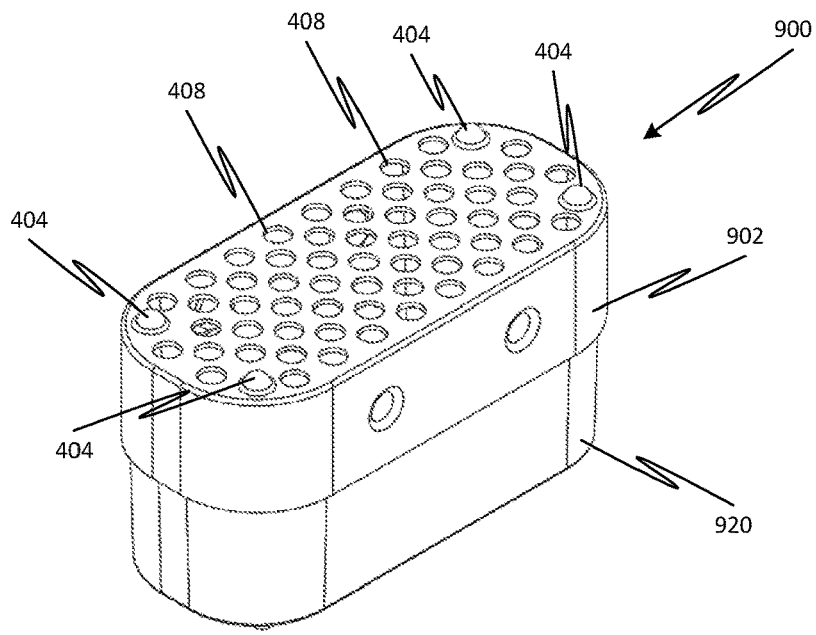
FIG. 9A is an isometric view of a capsule according to a first variation of the second embodiment.
Figure 9B:
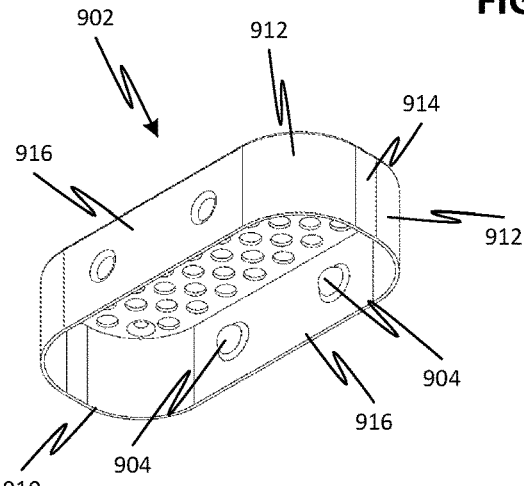
FIGS. 9B-9C are isometric and cross-sectional views of a cap of the capsule of FIG. 9A.
Figure 9C:
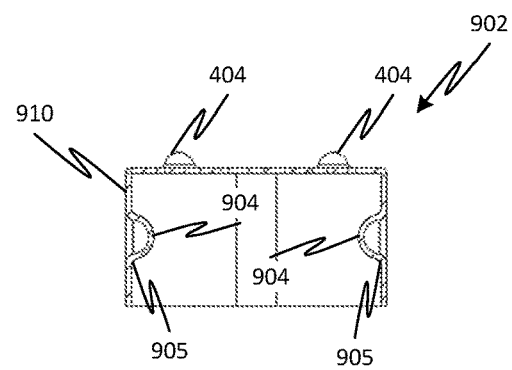
Figure 9D:
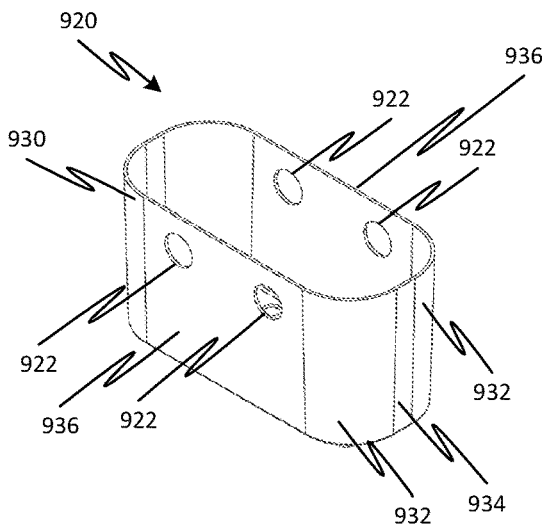
FIG. 9D is an isometric view of the cup of the capsule of FIG. 9A.
Figure 9E:
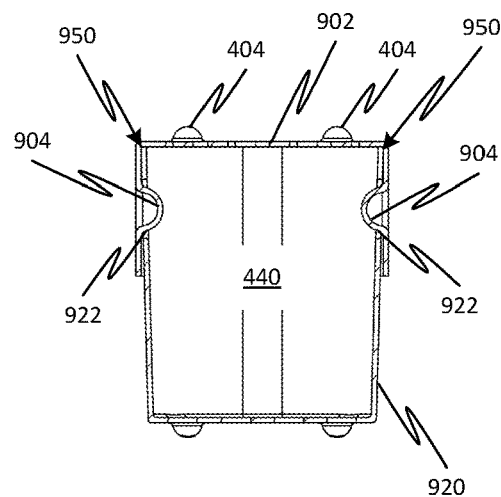
FIG. 9E is a cross-sectional view of the capsule of FIG. 9A, showing the tamper-resistant interaction between the cap and the cup.

The cup 920 can have a vertically extending sidewall 930 (peripheral sidewall) extending from a periphery of its vented surface to define recess 440. The cup sidewall 930 can have substantially flat portions 934 and 936 connected together by intervening curved portions 932. Along at least one of the flat portions, e.g., longer flat portions 936, is formed a pair of through-holes 922. The cap 902 and the cup 920 are constructed such that the cap protrusions 904 snap into or engage with the cup through-holes 922 once the cup 920 is fully inserted into the cap 902, as illustrated in FIG. 9E. In this manner, the combination of protrusions 904 and through-holes 922 act as tamper-resistant features to couple the cap 902 to the cup 920 and inhibit separation of the capsule 900. Alternatively or additionally, the cap 902 can be designed to form a press fit with lip 950 at a top of the cup sidewall 930 when the cup 920 is fully inserted into the cap 902, as with the first embodiment.

FIGS. 10A-10E show various views of an exemplary capsule 1000 according to a second variation of the second embodiment. Capsule 1000 includes a cap 1002 and a cup 1020 that fit together to form an enclosed interior volume 440. Depending from a periphery of the vented surface of the cap 1002 is a vertically extending sidewall 1010 (peripheral skirt), which has substantially flat portions 1014 and 1016 connected together by intervening curved portions 1012. Along at least one of the flat portions, e.g., longer flat portions 1016, is formed a pair of inwardly angled flanges 1004. For example, each flange 1004 can be formed in the respective flat portion 1016 by stamping.

The cup 1020 has a vertically extending sidewall 1030 (peripheral sidewall) depending from a periphery of its vented surface and can define recess 440. The cup sidewall 1030 has substantially flat portions 1034 and 1036 connected together by intervening curved portions 1032. Along at least one of the flat portions, e.g., longer flat portions 1036, is formed a pair of through-holes 1024. The cap 1002 and the cup 1020 are constructed such that the cap flanges 1004 snap into or engage with the cup through-holes 1024 once the cup 1020 is fully inserted into the cap 1002, as illustrated in FIG. 10D. Alternatively or additionally, the cap 1002 can be designed to form a press fit with lip 1050 at a top of the cup sidewall 1030 when cup 1020 is fully inserted into cap 1002, as with the first embodiment.

Moreover, in the second variation of the second embodiment, the cap 1002 can have a height ($H_{cap}$) that is almost as large as (e.g., at least 90% of) the height ($H_{cup}$) of the cup 1020. Alternatively, the cap 1002 and the cup 1020 can have substantially the same height, such that no portion of the cup sidewall 1030 is exposed once the cup 1020 is fully inserted into the cap 1002. With such relationships between the heights of the cap and cup, the tamper resistance of the capsules may be improved. Such height relationships may also be applied to the other disclosed embodiments, such as the first embodiment of FIGS. 4A-7C and the first variation of the second embodiment of FIGS. 9A-9E.

Although FIGS. 8A-10E illustrate the cap with protrusions and the cup with receptacles, other configurations are also possible according to one or more contemplated embodiments. For example, the cap may be provided with receptacles and the cup may be provided with protrusions. Alternatively, the cap and the cup may each include protrusions and receptacles, with the protrusions of one fitting into (or otherwise engaging with) the receptacles of the other. Moreover, although FIGS. 8A-10E illustrate a particular type of protrusion and receptacle, embodiments are not limited thereto. For example, although the receptacles illustrated in FIGS. 8A-10E are through-holes, it is also possible for receptacle to be a recess or indentation in a surface of the sidewall. It is also possible to locate the protrusions/receptacles on different portions of the sidewalls than those illustrated in FIGS. 9A-10E, for example, on the shorter flat portions rather than the longer flat portions. Moreover, although two tamper-resistant features are shown per side of the capsule in FIGS. 9A-10E, other numbers of tamper-resistant features are also possible.

Although holes in the vented surfaces of the capsule have been illustrated as a regular array of round holes in FIGS. 4A-10E and 11B, other shapes and arrangements for the holes of the vented surfaces of the capsule are also possible according to one or more contemplated embodiments. In particular, the arrangement, shape, and size of the holes of the vented surfaces are selected to maximize percent open area while maintaining device integrity and vaporizable material retention (i.e., preventing material contained within the capsule from easily escaping the capsule via the vented surfaces) and in consideration of the limits of the particular fabrication techniques.

Although the holes are illustrated in FIGS. 4A-10E and 11B as being uniform in size and distribution across the vented surfaces of the capsule, it is also possible for the holes to be non-uniformly distributed or non-uniformly sized. For example, the size and/or distribution of holes in different portions of each vented surface can be tailored in order to encourage air to flow through the capsule in a desired manner.

In any of the disclosed embodiments, the capsule can be formed of a heat-conductive material that allows for heating of the contained vaporizable material, while also avoiding contamination of the vaporizable material before and during vaporization. Material selection may also take into account ease of fabrication and material strength, in which case, food-safe-grade stainless steel 304 has been found advantageous when employing a drawing or stamping process. However, other fabrication methods are also contemplated, such as metal injection molding, and other metal materials, such as medical-grade stainless steel 316, may be preferable, for example, when employing other fabrication methods.

The dimensions and sizes of the disclosed capsules can be adapted to the dimensions of the particular oven of the personal vaporization device, which can vary in size and shape from those ovens specifically illustrated herein. In particular, the capsule is designed to maximize the enclosed area containing vaporizable material and to allow for rapid heating, while still being easily manufacturable. Thus, the wall thickness of the capsule is chosen to be thick enough to undergo fabrication without issue (e.g., to be drawn or stamped without cracking or tearing) while being sufficiently thin to provide a low thermal mass for rapid heating.

For example, illustrative capsules for use in the PAX brand vaporizers and made of stainless steel 304 can have an overall height ranging from 6.35 mm (0.25 in.) to 19.05 mm (0.75 in.) (in a first direction perpendicular to the vented surfaces), an overall length ranging from 10.16 mm (0.4 in.) to 19.05 mm (0.75 in.) (in a second direction parallel to the vented surfaces), an overall width ranging from 5.59 mm (0.22 in.) to 12.7 mm (0.5 in.) (in a third direction parallel to the vented surfaces and perpendicular to the second direction), a wall thickness of about 0.18 mm (0.007 in.), and/or an enclosed interior volume of about 1.15 cm$^3$ (0.07 cubic inches).

The size of the capsule can also be adapted to provide a substantially sliding fit at the bottom edge of the cap of the capsule, while still allowing the capsule to be removed from the oven (i.e., avoiding press fit conditions). In embodiments, the cap of the capsule has cross-dimensions in plan view with tolerance that yields no more than a 0.5 mm difference from the corresponding cross-dimensions of the opening defined by the oven sidewall at a height of the bottom edge of the cap of the inserted capsule. For example, when the opening of the oven at a height corresponding to the position of the bottom edge of the cap (e.g., 303 in FIG. 3A) has cross-dimensions in plan view of 8.83±0.15 mm by 19.04±0.11 mm, the bottom edge of the cap of the capsule has cross-dimensions in plan view of 8.60±0.08 mm by 18.80±0.13 mm. The substantially sliding fit (or seal) provided by the interaction between the cap and the oven sidewall can force more, and preferably substantially all, of the air to flow through the capsule rather than around the capsule.

In one or more first exemplary configurations, a capsule for use in a personal vaporization device comprises a cap, a cup, a first standoff structure, and a second standoff structure. The cap has a first base wall and a peripheral skirt. The first base wall has a plurality of holes (e.g., air inlet or air outlet holes) extending from a first surface to a second surface of the first base wall. The peripheral skirt extends from the second surface of the first base wall. The cup has a second base wall and a peripheral sidewall. The second base wall has a plurality of holes (e.g., air outlet or air inlet holes) extending from a third surface to a fourth surface of the second base wall. The peripheral sidewall extends from the third surface of the second base wall. The first standoff structure is at a first surface side of the first base wall. The second standoff structure is at a fourth surface side of the second base wall. The cap and the cup are coupled together and enclose an interior volume for holding a vaporizable material between the first base wall and the second base wall. The first and second standoff structures are constructed to space the first base wall and the second base wall, respectively, from facing portions of the personal vaporization device (e.g., the vaporization chamber formed by walls of the oven and/or lid of the vaporization device).

In the first exemplary configurations or any other configuration or embodiment, the first standoff structure or the second standoff structure is integrated with or forms a part of the cap or cup.

In the first exemplary configurations or any other configuration or embodiment, a portion of the peripheral skirt adjacent the first base wall engages with a lip portion of the peripheral sidewall to mechanically couple the cap to the cup.

In the first exemplary configurations or any other configuration or embodiment, the peripheral skirt and/or the peripheral sidewall are each substantially continuous structures without any through-holes therein.

In the first exemplary configurations or any other configuration or embodiment, the first standoff structure comprises one or more feet formed on and extending from the first surface of the first base wall, and/or the second standoff structure comprise one or more feet formed on and extending from the fourth surface of the second base wall.

In the first exemplary configurations or any other configuration or embodiment, the second standoff structure comprises a continuous annular rib formed on and extending from the fourth surface of the second base wall.

In the first exemplary configurations or any other configuration or embodiment, one of the peripheral skirt and the peripheral sidewall has a protrusion that interacts with a receptacle of the other of the peripheral skirt and the peripheral sidewall to resist separation of the cap from the cup. For example, the protrusion comprises a dimpled portion of the peripheral skirt, and the receptacle comprises a cooperating recess disposed to receive the dimpled portion. In another example, the protrusion comprises an inwardly-angled flange of the peripheral skirt, and the receptacle comprises a cooperating recess or through hole into which the flange extends.

In the first exemplary configurations or any other configuration or embodiment, a height of the peripheral skirt in a direction perpendicular to the first base wall can be less than a height of the peripheral sidewall in a direction perpendicular to the second base wall.

In the first exemplary configurations or any other configuration or embodiment, a height of the peripheral skirt in a direction perpendicular to the first base wall can be greater than a height of the peripheral sidewall in a direction perpendicular to the second base wall, such that the second standoff structure is formed by a portion of the peripheral skirt extending beyond the second base wall of the cup.

In the first exemplary configurations or any other configuration or embodiment, the capsule further comprises vaporizable material held within an interior volume between the first base wall and the second base wall.

In one or more second exemplary configurations, a capsule for use in a personal vaporization device comprises means for spacing opposing base walls of the capsule from facing portions of the personal vaporization device (e.g., the vaporization chamber formed by walls of the oven and/or lid of the vaporization device), where the opposing base walls each have a plurality of through holes therein.

In the second exemplary configurations or any other configuration or embodiment, the capsule further comprises tamper-resistant means for resisting opening of the capsule to access its internal volume of vaporizable material.

In one or more third exemplary configurations, a vaporization system comprises an oven, a lid, and a capsule according to the first or second exemplary configurations or any other configuration or embodiment. The oven and lid may be parts of a personal or portable vaporization device. The oven and the lid define a vaporization chamber.

In the third exemplary configurations or any other configuration or embodiment, the oven has a bottom wall, an outlet, an upper inlet portion opposite the bottom wall, and a sidewall extending between the bottom wall and the inlet portion.

In the third exemplary configurations or any other configuration or embodiment, the lid is disposed within the inlet portion, and the lid is constructed and disposed to allow air to be drawn into the vaporization chamber via the inlet portion In the third exemplary configurations or any other configuration or embodiment, the lid may be removable from the vaporization device, for loading/unloading of the capsule to/from the vaporization chamber.

In the third exemplary configurations or any other configuration or embodiment, a shape of an outer perimeter of the capsule in plan view is the same as that of an inner perimeter of the oven in plan view.

In the third exemplary configurations or any other configuration or embodiment, the peripheral skirt of the cap makes a substantially sliding fit with the oven sidewall.

In the third exemplary configurations or any other configuration or embodiment, a gap between the capsule (e.g., its peripheral sidewall) and the oven sidewall is such that more air flows through an interior volume of the capsule en route to the outlet than flows through the gap en route to the outlet.

In the third exemplary configurations or any other configuration or embodiment, the capsule substantially follows a profile of the oven sidewall in cross-sectional view.

In one or more fourth exemplary configurations, a kit is provided for assembling a capsule according to one or more of the first exemplary configurations. The kit comprises the cap and the cup, which is separate from the cap. The first peripheral sidewall of the cup is constructed to be inserted into the cap during the assembling such that the first peripheral sidewall is received within the first peripheral skirt to couple the cap and the cup together.

In one or more fifth exemplary configurations, a kit is provided for assembling a capsule according to one or more of the second exemplary configurations. The kit comprises a first capsule part having one of the opposing base walls, and a second capsule part having another of the opposing base walls and being separate from the first capsule part. The first and second capsule parts are constructed to be coupled together.

Beyond the example capsules and vaporization systems shown and discussed herein, many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A capsule for use in a personal vaporization device, the capsule comprising:
 a cap having a first base wall with a plurality of holes extending through the first base wall, and a first peripheral skirt extending from the first base wall;
 a cup having a second base wall with a plurality of holes extending through the second base wall, and a first peripheral sidewall extending from the second base wall;
 a first standoff structure on a side of the first base wall opposite the first peripheral skirt; and
 a second standoff structure on a side of the second base wall opposite the first peripheral sidewall,
 wherein the cap and the cup are coupled together and enclose an interior volume for holding a vaporizable material between the first base wall and the second base wall, and
 the first and second standoff structures are constructed to space the first base wall and the second base wall, respectively, from adjacent surfaces of the personal vaporization device.

2. The capsule according to claim 1, wherein a portion of the first peripheral skirt adjacent to the first base wall engages with a lip portion of the first peripheral sidewall to mechanically couple the cap to the cup.

3. The capsule according to claim 1, wherein the first peripheral skirt is a substantially continuous structure without any holes therein.

4. The capsule according to claim 1, wherein the first peripheral sidewall is a substantially continuous structure without any holes therein.

5. The capsule according to claim 1, wherein the first standoff structure comprises one or more feet extending from a surface of the first base wall that is opposite from the first peripheral skirt.

6. The capsule according to claim 1, wherein the second standoff structure comprises one or more feet extending from a surface of the second base wall that is opposite from the first peripheral sidewall.

7. The capsule according to claim 1, wherein the second standoff structure comprises a continuous annular rib extending from a surface of the second base wall that is opposite from the first peripheral sidewall.

8. The capsule according to claim 1, wherein one of the first peripheral skirt and the first peripheral sidewall has a projecting surface that engages with a receptacle of the other of the first peripheral skirt and the first peripheral sidewall so as to resist separation of the cap from the cup.

9. The capsule according to claim 8, wherein the projecting surface comprises an inwardly-extending protuberance, and the receptacle comprises a hole or recess disposed to receive protuberance.

10. The capsule according to claim 8, wherein the projecting surface comprises an inwardly-angled flange, and the receptacle comprises a hole or recess into which a free end of the flange extends.

11. The capsule according to claim 1, wherein a height of the first peripheral skirt in a direction perpendicular to the first base wall is greater than a height of the first peripheral sidewall in a direction perpendicular to the second base wall, such that the second standoff structure is formed by a portion of the first peripheral skirt that extends beyond the second base wall of the cup.

12. The capsule according to claim 1, further comprising the vaporizable material held within the interior volume between the first base wall and the second base wall.

13. A kit for assembling a capsule according to claim 1, the kit comprising:
 the cap; and
 the cup, which is separate from the cap,
 wherein the first peripheral sidewall is constructed to be inserted into the cap during the assembling such that the first peripheral sidewall is received within the first peripheral skirt to couple the cap and the cup together.

14. A vaporization system comprising:
 an oven having a first wall with an outlet, an inlet portion opposite the outlet, and a sidewall extending between the first wall and the inlet portion;
 a lid provided at the inlet portion such that the oven and the lid define a vaporization chamber, the lid being constructed and disposed such that air is drawn into the vaporization chamber via the inlet portion when suction is applied to the outlet; and
 a capsule disposed in said vaporization chamber, the capsule comprising:
 a cap having a first base wall with a plurality of holes extending through the first base wall and a first peripheral skirt extending from the first base wall;
 a cup having a second base wall with a plurality of holes extending through the second base wall and a first peripheral sidewall extending from the second base wall;
 a first standoff structure on a side of the first base wall opposite the first peripheral skirt; and
 a second standoff structure on a side of the second base wall opposite the first peripheral sidewall,
 wherein the cap and the cup are coupled together and enclose an interior volume for holding a vaporizable material between the first base wall and the second base wall, and
 the first and second standoff structures are constructed to space the first base wall and the second base wall, respectively, from facing surfaces of the vaporization chamber.

15. The vaporization system according to claim 14, wherein a size and shape of an outer perimeter of the capsule in plan view is substantially the same as that of an inner perimeter of the oven at the inlet portion in plan view.

16. The vaporization system according to claim 14, wherein the first peripheral skirt of the cap makes a substantially sliding fit with the oven sidewall.

17. The vaporization system according to claim 14, wherein a gap between the first peripheral sidewall and the oven sidewall is such that more air flows through an interior volume of the capsule en route to the outlet than flows through the gap en route to the outlet when suction is applied to the outlet.

18. The vaporization system according to claim 14, wherein a portion of the first peripheral skirt adjacent to the first base wall engages with a lip portion of the first peripheral sidewall to mechanically couple the cap to the cup.

19. The vaporization system according to claim 14, wherein the first peripheral skirt is a substantially continuous structure without any holes therein.

20. The vaporization system according to claim 14, wherein the first peripheral sidewall is a substantially continuous structure without any holes therein.

21. The vaporization system according to claim 14, wherein the first standoff structure comprises one or more feet extending from a surface of the first base wall that is opposite from the first peripheral skirt, the one or more feet contacting a surface of the lid to space the first base wall of the cap from the lid.

22. The vaporization system according to claim 14, wherein the second standoff structure comprises one or more feet extending from a surface of the second base wall that is opposite from the first peripheral sidewall, the one or more feet contacting the first wall of the oven to space the second base wall of the cup from the oven.

23. The vaporization system according to claim 14, wherein the second standoff structure comprises a continuous annular rib extending from a surface of the second base wall that is opposite from the first peripheral sidewall, the continuous annular rib contacting the first wall of the oven to space the second base wall of the cup from the oven.

24. The vaporization system according to claim 14, wherein one of the first peripheral skirt and the first peripheral sidewall has a projecting surface that engages with a receptacle of the other of the first peripheral skirt and the first peripheral sidewall so as to resist separation of the cap from the cup.

25. The vaporization system according to claim 24, wherein the projecting surface comprises an inwardly-extending protuberance, and the receptacle comprises a hole or recess disposed to receive protuberance.

26. The vaporization system according to claim 24, wherein the projecting surface comprises an inwardly-angled flange, and the receptacle comprises a hole or recess into which a free end of the flange extends.

27. The vaporization system according to claim 14, wherein a height of the first peripheral skirt in a direction perpendicular to the first base wall is greater than a height of the first peripheral sidewall in a direction perpendicular to the second base wall, such that the second standoff structure is formed by a portion of the first peripheral skirt that extends beyond the second base wall of the cup to contact the first wall of the oven, thereby spacing the second base wall of the cup from the oven.

28. The vaporization system according to claim 14, further comprising the vaporizable material held within the interior volume between the first base wall and the second base wall.

* * * * *